United States Patent
Kariyama et al.

(10) Patent No.: US 10,995,326 B2
(45) Date of Patent: May 4, 2021

(54) METHOD FOR PRODUCING SUBSTRATE CULTURE PRODUCT AND SUBSTRATE CULTURE PRODUCT

(71) Applicant: FUJIWARA TECHNO-ART CO., LTD., Okayama (JP)

(72) Inventors: Masahiro Kariyama, Okayama (JP); Akira Mori, Okayama (JP); Satoko Takahashi, Okayama (JP)

(73) Assignee: FUJIWARA TECHNO-ART CO., LTD., Okayama (JP)

( * ) Notice: Subject to any disclaimer, the term of this patent is extended or adjusted under 35 U.S.C. 154(b) by 0 days.

(21) Appl. No.: 16/587,289

(22) Filed: Sep. 30, 2019

(65) Prior Publication Data

US 2021/0071154 A1    Mar. 11, 2021

(30) Foreign Application Priority Data

Sep. 9, 2019   (JP) .............................. JP2019-164037

(51) Int. Cl.
| | |
|---|---|
| *C12N 9/18* | (2006.01) |
| *C12N 15/74* | (2006.01) |
| *C12N 9/16* | (2006.01) |
| *A23K 10/18* | (2016.01) |
| *C12N 9/24* | (2006.01) |

(52) U.S. Cl.
CPC ............... *C12N 9/18* (2013.01); *A23K 10/18* (2016.05); *C12N 9/16* (2013.01); *C12N 9/2402* (2013.01); *C12N 9/2482* (2013.01); *C12N 15/74* (2013.01); *C12Y 301/0102* (2013.01); *C12Y 301/03* (2013.01); *C12Y 302/01008* (2013.01); *C12Y 302/01015* (2013.01)

(58) Field of Classification Search
CPC .................................. A23K 10/16; C12N 9/58
See application file for complete search history.

(56) References Cited

U.S. PATENT DOCUMENTS

2012/0142051 A1*   6/2012   Ogawa ................... C07K 14/38
                                                              435/69.1

FOREIGN PATENT DOCUMENTS

JP       2007-325580 A       12/2007

OTHER PUBLICATIONS

Suzuki et al., "Production of Polygalacturonase by Recombinant Aspergillus oryzae in Solid-State Fermentation Using Potato Pulp", Food Science and Technology Research, vol. 16, No. 5, pp. 517-521.*

* cited by examiner

*Primary Examiner* — Suzanne M Noakes
(74) *Attorney, Agent, or Firm* — Pearne & Gordon LLP

(57) ABSTRACT

Provided is a method for safely and selectively producing a substrate culture product including a large amount of a desired degrading enzyme. A method for producing a substrate culture product used for feedstuff includes inoculating filamentous fungi bred so that a target degrading enzyme is produced by self-cloning in high productivity on a substrate, and producing the substrate culture product having functionality by ventilating the substrate to carry out solid culture.

12 Claims, 5 Drawing Sheets

Specification includes a Sequence Listing.

Expression Cassette 1

Expression Cassette 2

Expression Cassette 3

Expression Cassette 4

Expression Cassette 5

First Genetic Transformation

Second Genetic Transformation

METHOD FOR PRODUCING SUBSTRATE CULTURE PRODUCT AND SUBSTRATE CULTURE PRODUCT

FIELD

The present invention relates to a method for producing a substrate culture product and the substrate culture product.

BACKGROUND

A technique in which specific fungi are inoculated on a substrate such as brown rice and cultured and the cultured product is used for feedstuff of animals has been known.

Patent Literature 1 describes that an Aspergillus oryzae-IK-05074 strain is inoculated on brown rice and solid-cultured and the solid-cultured product is mixed in feedstuff to be ingested to chickens. It is described in Patent Literature 1 that the ingestion of the solid-cultured product to animals allows proliferation of disease-causing bacteria and coccidia in the intestine in the animals to be reduced and infectious disease to be prevented. It is said that the above-described fungi have excellent ability to produce acid resistant a-amylase.

CITATION LIST

Patent Literature

Patent Literature 1: Japanese Patent Application Laid-open No. 2007-325580

SUMMARY

Technical Problem

Degrading enzymes effective to improve the digestion ratio of feedstuff vary depending on the kinds of animals eating the feedstuff or the characteristics of the feedstuff such as raw materials used for the feedstuff. For example, feedstuff for cows or chickens has different formulations. In addition, pH of stomach fluids differs and accumulated time in the stomach also differs.

In Patent Literature 1, specific fungi are inoculated on brown rice or the like and proliferate and then the specific fungi or the acid resistant α-amylase produced by the specific fungi are/is in contact with animals. In the method according to Patent Literature 1, only the activity of the acid resistant α-amylase is improved and the effect of improving the digestion ratio of the feedstuff is restrictive.

A method for highly expressing a desired enzyme by microorganisms utilizing gene manipulation can also be considered. However, in the case where the gene introduced to the microorganisms is essentially different from the genomic gene of the microorganisms, safety evaluation is required.

An object of the present invention is to provide a method for safely and selectively producing a substrate culture product including a desired degrading enzyme in a high content.

Solution to Problem

The above-described problems are solved by a method for producing a substrate culture product used for feedstuff, the method including inoculating filamentous fungi bred so that a target degrading enzyme is produced by self-cloning in high productivity on a substrate, and producing the substrate culture product having functionality by ventilating the substrate to carry out solid culture.

In the method for producing the substrate culture product, the filamentous fungi are preferably fungi not producing mold poison. In the method for producing the substrate culture product, the fungi not producing mold poison are Aspergillus oryzae, Aspergillus sojae, or Aspergillus luchuensis.

In the method, the solid culture is preferably carried out by controlling substance temperature by adjusting at least one of temperature and humidity of air supplied to the substrate.

In the method, a water content of the substrate culture product is preferably adjusted by sprinkling water or drying.

In the method, the substrate culture product preferably includes polysaccharides constituting hyphae of the filamentous fungi.

The method may be a method for further including extracting components including the target enzymes from the substrate culture product produced by the above-described method.

The method may further includes mixing the substrate culture product produced by the above-described method or the extract produced by the above-described method and a new substrate for which culture is not carried out.

By the method, a solid-form substrate culture product including hyphae of the filamentous fungi bred so that target degrading enzymes are produced by self-cloning in high productivity and the target enzymes produced by the filamentous fungi can be produced.

Advantageous Effects of Invention

According to the present invention, a method for safely and selectively producing a substrate culture product including a desired degrading enzyme in a high content can be provided. For example, when the target degrading enzyme promotes the digestion of the feedstuff, the digestion ratio of the feedstuff is improved due to the action of the degrading enzymes by feeding the produced substrate culture product to animals as the feedstuff. The substrate culture product includes the polysaccharides that constitute the hyphae of the filamentous fungi and thus improvement in the immune strength of the animals ingesting the substrate culture product is expected when the substrate culture product including the polysaccharides and the filamentous fungi are ingested together.

DESCRIPTION OF EMBODIMENTS

Figure 1:
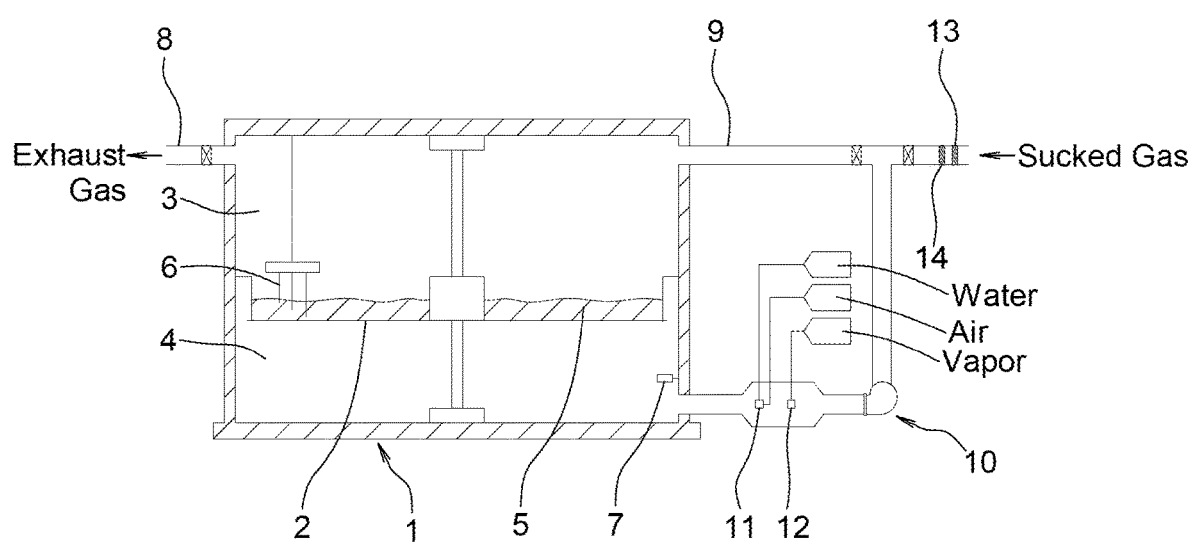
FIG. 1 is a view illustrating one example of a solid culture apparatus used in the method for producing the substrate culture product.

Hereinafter, suitable embodiments for carrying out the present invention will be described.

The present invention includes a method for producing a substrate culture product used for feedstuff, the method including: inoculating filamentous fungi bred so that a target degrading enzyme is produced by self-cloning in high productivity on a substrate, and producing the substrate culture product having functionality by ventilating the substrate to carry out solid culture.

The substrate may be a solid organic substance suitable for the filamentous fungi to breed. The solid shall include, in addition to a solid content having hardness, a slurry-like substance or a powder or grains. Examples of the substrate include one or more organic substances selected from the group consisting of cereals such as barleycorn, wheat, the bran of wheat, rice, beans, and corn; residues of processed food such as beet pulp, the squeezed lees of oil, and the squeezed lees of fermented foods; and food residue such as leftover foods. Examples of the squeezed lees of oil include the squeezed lees of soybean, the squeezed lees of rapeseed, the squeezed lees of sesame, and the squeezed lees of corn. Examples of the squeezed lees of the fermented foods include sake lees and soy sauce lees.

Of the substrates described above, the squeezed lees formed after squeezing oil from rapeseed (hereinafter referred to as rapeseed lees) have worse digestion efficiency than the digestion efficiency of the squeezed lees formed after squeezing oil from soybean (hereinafter referred to as soybean lees) and thus have a lower value as the feedstuff than the value of the soybean lees. The rapeseed lees include a substance that inhibits the absorption of specific nutritional components and thus a feeding amount is restricted. It can be expected that the digestion efficiency of the rapeseed lees is improved and the substance inhibiting the absorption of the specific nutritional components is reduced to ease the feeding restriction by blending the substrate culture product produced by self-cloning the target degrading enzyme in high productivity to the feedstuff including the rapeseed lees. This operation improves the value as feedstuff that conventionally has a low value such as the rapeseed lees.

The filamentous fungi that are harmless to animals ingesting the filamentous fungi and proliferates using the substrate as a nutrition source may be used. Examples of such filamentous fungi include fungi not producing mold poison. As the fungi not producing mold poison, for example, fungi cells that do not express a gene related to production of the mold poison and thus lose the production ability of the mold poison by variation and deficit of the gene related to the biosynthesis of the mold poison or the accumulation of genetic factor such as transcription suppression can be suitably used. Examples of the fungi not producing mold poison include *Aspergillus oryzae, Aspergillus sojae,* or *Aspergillus luchuensis.* As these filamentous fungi, seed fungi for the fermentation of fermented foods are commercially available or the filamentous fungi can be issued from NITE Biological Resource Center (NBRC). The genome or the like of such filamentous fungi can be used as a template for self-cloning and can be used as a host to which the self-cloning gene is introduced.

Examples of the mold poison include aflatoxin, deoxynivalenol, ochratoxin, fumonisin, zearalenone, patulin, sterigmatocystin, and fusarium toxin.

Any degrading enzymes may be used as long as arbitrary substances included in the substrate or the feedstuff are degraded to a substance having lower molecular weight than that of the arbitrary substances and some sort of functionality may be provided to the substrate culture product. The substrate culture product refers to the culture product of the substrate. Examples of the degrading enzyme include one or more enzymes selected from the group consisting of amylase, alkaline protease, acidic protease, neutral protease, xylanase, β-glucanase, cellulase, tannase, phytase, lactase, lipase, pectinase such as polygalac-turonase, a xylanase-pectinase complex enzyme, and a cellulase-protease-pectinase complex enzyme.

Functionality is provided to the substrate culture product by the action of filamentous fungi. Actualized functionality varies depending on the degrading enzyme produced by the self-cloning in high productivity.

For example, in the case where the target degrading enzyme is phytase, phytase catalyzes the chemical reaction in which inorganic form phosphoric acid is separated from phytic acid included in the feedstuff and the like. It is said that phytic acid inhibits absorption of minerals such as calcium and zinc included in the feedstuff into the body of an aminol ingesting the feedstuff. Therefore, degradation of phytic acid with phytase improves the absorption ratio of minerals. Phosphorous generated by degradation of phytic acid is also absorbed into the body of the animals ingesting the feedstuff.

For example, in the case where the target degrading enzyme is tannase, tannase catalyzes the chemical reaction in which tannin included in the feedstuff or the like is degraded. Some types of tannin form complexes by strongly bonding to polymers such as proteins. Tannin may exist in the state of being intricately entangled with the components constituting the cell walls of plants and may inhibit degradation of the cell walls. It is considered that degradation of tannin with tannase improves the degradation efficiency of the cell walls of plant raw materials included in the feedstuff and thus the feedstuff becomes easily digested. Tannin has also been known as a bitter component. The degradation of tannin results in reducing astringent taste and thus the taste of the feedstuff is improved.

For example, in the case where the target degrading enzymes are cellulase, pectinase, and the like, these degrading enzymes catalyze the reaction in which cellulose, pectin, and the like included in the feedstuff or the like are degraded. Polysaccharides such as cellulose and pectin are a kind of the component constituting the cell walls of plants. Various kinds of the polysaccharides constituting the cell walls of plants have been known. The forms thereof are various and the constitutions are complex. In order to efficiently degrade the cell wall polysaccharide having complex structures, the degrading enzymes preferably act stepwise. For example, degradation efficiency of the cell walls of plant raw material included in the feedstuff is improved by degrading cellulose, pectin, and the like with the enzymes such as cellulase and pectinase. Consequently, the feedstuff becomes easily digested.

The degrading enzymes can be classified into digestion-promoting enzymes such as xylanase, pectinase, amylase, alkaline protease, β-glucanase, protease, cellulase, lactase, or lipase assisting the digestion of the feedstuff and inhibitor-degrading enzymes such as tannase and phytase degrading substances that inhibit the absorption of arbitrary substances.

As the degrading enzyme, at least one enzyme may be produced in high productivity and two or more of enzymes are preferably produced in high productivity. For example, in the case where the feedstuff is fed to animals, a plurality of types of feedstuff are mixed and the mixed feedstuff is fed. The types of the effective degrading enzymes for digestion of the mixed feedstuff may vary depending on the types of the feedstuff. Therefore, digestion efficiency can be improved by producing two or more enzymes in high productivity depending on the types of the feedstuff to be mixed. For example, as described above, the cell walls of the plant raw material included in the feedstuff have the complex structure and thus the degrading enzymes sequentially act on and degrade the cell walls stepwise to become a form that is easily digested in animals. The cell walls can be easily degraded by producing two or more of the enzymes effective for degradation of the cell walls in high productivity.

As the above-described example, the components in the feedstuff are easily and effectively digested and absorbed when animals ingest the feedstuff by producing the two or more of the enzymes in high productivity. The functionality of the substrate culture product used as the feedstuff can be further improved by producing the degrading enzymes in various combinations in high productivity. As a matter of course, the enzymes produced in high productivity also synergistically act to various enzymes originally produced by the filamentous fungi. Consequently, the more types of the enzymes produced in high productivity, the more synergistic effect is obtained.

As the filamentous fungi, filamentous fungi bred so that the target degrading enzyme is produced by self-cloning in high productivity are used. The self-cloning refers to a cloning technique in which species from which an incorporated gene sequence is obtained and species of the host to which the gene sequence is incorporated are the same in terms of taxonomy. Therefore, the genetically modified product obtained by the self-cloning is essentially the same as naturally-occurring species and is distinguished from the other genetically-modified products and thus is excluded from safety confirmation. Usually, in the case where the genetically-modified product is used in industry, containment measures for preventing the genetically-modified product from outflow to nature are required. However, the genetically-modified product obtained by the self-cloning can skip the containment measures of the genetically-modified product. Consequently, the self-cloning has an advantage that the cost for facilities can be remarkably reduced.

The self-cloning technology is different from other gene-modifying technology and is the gene-modifying technology for which safety is approved. Use of the self-cloning allows the filamentous fungi having the target characteristics to be bred in a short period of time in accordance with the types of the feedstuff and the characteristics such as the digestion mechanism of animals to which the feedstuff is ingested; and the substrate culture product that the target degrading enzymes is highly produced or the target enzyme itself to be mass-produced highly efficiently and safely.

The method for the self-cloning may be a method of introducing the gene sequence of fungi that are the same species in terms of taxonomy as the target filamentous fungi to which the gene sequence is incorporated into the filamentous fungi serving as the host, and may be the method producing the target degrading enzyme in high productivity. When the target gene sequence is introduced into the filamentous fungi, the target gene sequence may be introduced into plasmid and the plasmid may be introduced into the filamentous fungi, or the cassette for high expression described below may be introduced into the filamentous fungi.

Examples of the method for the self-cloning include a method for carrying out genetic transformation of the cassette for high expression including a promoter sequence for high expression, the gene of the target degrading enzyme, and a terminator sequence to the filamentous fungi. At the time of carrying out the genetic transformation, a marker gene for selectively culturing the transformant may also be co-translated. In the preparation of the cassette for high expression or the marker gene, for example, PCR is preferably used.

In order to produce the target degrading enzyme with the filamentous fungi in high productivity, for example, the promoter sequence for high expression, the terminator sequence, or the marker gene may be used. In this case, the promoter sequence, the terminator sequence, or the marker gene originated from fungi that are the same spices as the filamentous fungi in terms of taxonomy is also used.

In order to clone the target degrading enzyme, the promoter sequence, and the like by the self-cloning, for example, a desired gene sequence may be amplified by PCR using the genomic DNA of the filamentous fungi as a template or a desired gene sequence may be amplified by PCR using the cDNA as a template.

The cassette for high expression having the above-described promoter sequence, target degrading enzyme gene, and terminator sequence is preferably prepared by the following manner. When conducting the self-cloning, as for the promoter sequence, a sequence as corresponding to the promoter sequence is designed as a sense primer in the 5'-terminal side. A sequence as corresponding to the promoter sequence is also designed as an antisense primer in the 3'-terminal side. Similarly, when conducting the self-cloning, as for the terminator sequence, a sequence as corresponding to the terminator sequence is also designed as a sense primer in the 5'-terminal side. As an antisense primer in the 3'-terminal side, a sequence as corresponding to the terminator sequence is also designed. When conducting the self-cloning, as for the target degrading enzyme, a primer in which the sequence of 5 to 40 base pairs is added to the sequence corresponding to the target degrading enzyme so that the sequence overlaps to the sequence in the downstream side of the promoter is designed as a sense primer in the 5'-terminal side. As an antisense primer in the 3'-terminal side, a primer in which the sequence of 5 to 40 base pairs is added to the sequence corresponding to the target degrading enzyme so that the sequence overlaps to the sequence in the upstream side of the terminator is designed. Using thus designed each of the primers, the promoter sequence, the target degrading enzyme gene, and the terminator sequence are amplified, and mixed. Using the mixture as a template, for example, fusion PCR is carried out using the sense primer in the 5'-terminal side used in the amplification of the promoter sequence and the antisense primer in the 3'-terminal side used in the amplification of the terminator sequence. This operation allows the cassette for high expression in which the promoter sequence, the target degrading enzyme, and the terminator sequence are joined to be amplified. Here, in the case where the terms "5'-terminal side" and "3'-terminal side" are used, the sense chain is used as the reference. In the case where the term "sense primer" is used, the term refers to a primer for annealing to an antisense chain, whereas in the case where the term "antisense primer" is used, the term refers to a primer for annealing to a sense chain.

In the above-described example, the overlapping sequence is provided in the target degrading enzyme. The overlapping sequence may be provided at the 3'-terminal of the promoter sequence or the 5'-terminal of the terminator sequence.

The number of the genes introduced into the filamentous fungi by the self-cloning is not limited. For example, a plurality of genes coding the degrading enzymes to the filamentous fungi may be introduced so that a plurality of functionalities is expressed by the combination of the degrading enzymes.

The solid culture is carried out by inoculating the spores of the filamentous fungi bred by the self-cloning to the substrate while the substrate is ventilated with air in which at least one of temperature and humidity is adjusted. The temperature control of the substrate during the culture may be carried out by wind temperature control or substance temperature control. According to the wind temperature control, air having a constant temperature is supplied and ventilated through the substrate. According to the substance temperature control, temperature of air supplied and ventilated throguth the substrate is changed depending on the temperature of the substrate. The solid culture can be carried out by adjusting at least one of temperature and humidity of the ventilating air using at lease one of the temperature control and a humidity control.

A solid culture apparatus preferably includes, for example as illustrated in FIG. 1, a culture chamber 1 having a culture bed 2 inside the culture chamber 1 on which the substrate 5 is accumulated and an air-conditioning apparatus 10 that can blow temperature and/or humidity-conditioned air from the lower side of the culture bed 2. The culture chamber 1 is separated into an upper chamber 3 and a lower chamber 4 by the culture bed 2. A plurality of open holes are provided through the culture bed 2. The air supplied from the air-conditioning apparatus 10 is fed to the lower chamber 4, passes through the open holes to pass in the spaces between a plurality of substrates and goes through the upper chamber 3. A substance temperature sensor 6 for measuring the temperature of the substrate is provided in the upper chamber 3 and a humidity sensor 7 for measuring the humidity of the air fed to the lower chamber 4 is provided in the lower chamber 4.

The solid culture apparatus may discharge the partial or entire air to the outside through an exhaust gas duct 8 or may circulate the partial or entire air through a circulation duct 9 when air is supplied to the substrate 5.

The air-conditioning apparatus 10 of the solid culture apparatus preferably has a structure including a two-fluid nozzle 11 for controlling humidity and vapor nozzle 12 for controlling temperature. In addition, a cooling part 13 or a heating part 14 may be included. The cooling part may be a cooling part that can cool sucked gas. For example, a heat exchangerinside which a coolant passes may be exemplified. The heating part may be a heating part that can heat sucked gas. For example, a heat exchanger inside which a heating medium passes or a heater may be exemplified. Examples of the heat exchanger include a finned tube heat exchanger. Examples of the coolant include liquid such as cold water or a gas such as coolant gas. Examples of the heating medium include liquid such as warm water, gas such as hot air, or vapor.

The solid culture is carried out by inoculating the spores of the filamentous fungi bred by the self-cloning to the substrate, placing the inoculated substrate on the culture bed of the solid culture apparatus, and ventilating the substrate with air in which temperature and/or humidity are strictly controlled. In the process of the proliferation of the filamentous fungi to produce the enzyme, the substance temperature of the substrate changes depending on the culture process. Therefore, in order to promote the culture in a desired substance temperature process, the solid culture is preferably carried out by adjusting at least one of the temperature and the humidity of air supplied to the substrate. This allows the temperature and humidity during the culture to be accurately controlled and the production of the target degrading enzyme in high productivity to be promoted by efficiently proliferating the filamentous fungi while the proliferation of unwanted fungi is being reduced.

Figure 2:
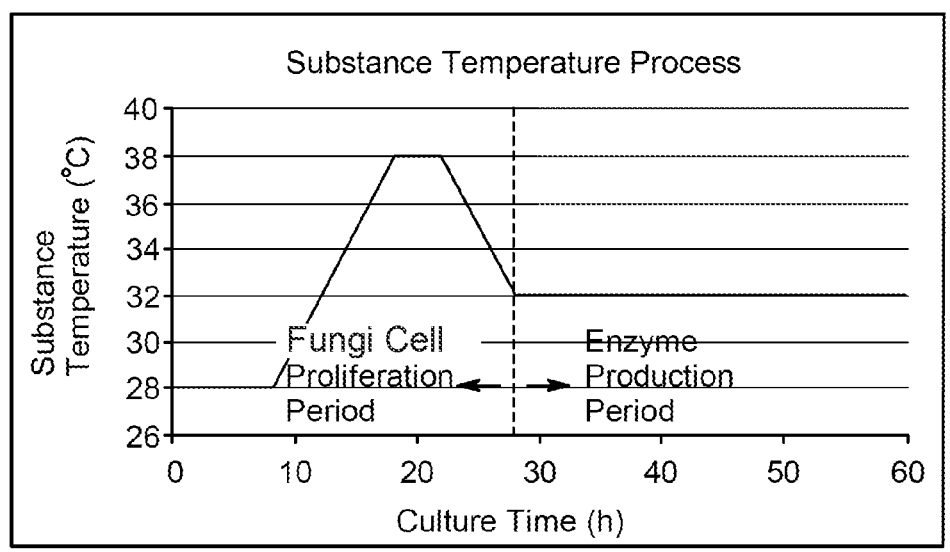
FIG. 2 is a graph illustrating one example of relationship between substance temperature of the substrate and passage of time.

When the filamentous fungi produce the enzyme, the kind of the produced enzyme varies depending on the temperature. In particular, in order to produce the target degrading enzyme in higher productivity, the substance temperature process in the enzyme production period of the filamentous fungi is important. The enzyme production period is a period continuing after the fungi cell proliferation period of the filamentous fungi and appears in the latter half of the solid culture. For distinguishing between the fungi cell proliferation period and the enzyme production period of the filamentous fungi, for example as illustrated in FIG. 2, the heat generation of the filamentous fungi associated with the fungi cell proliferation is one indication. In this example, the fungi cell proliferation period exists after the peak of the heat generation associated with the fungi cell proliferation of the filamentous fungi and before the period of stabilizing the substance temperature and the enzyme production period exists after the above-described period. For example, the substance temperature of the substrate in the enzyme production period of the filamentous fungi can be set to 18° C. to 50° C. and is preferably 18° C. to 34° C. or 35° C. to 50° C.

The solid culture is preferably carried out by inoculating the spores of the filamentous fungi bred by the self-cloning to the substrate and adjusting the water content of the substrate culture product by sprinkling water or drying. The sprinkling of water or drying may be carried out during the solid culture, or may be carried out after the completion of the solid culture. The adjustment of the water content included in the substrate during the solid culture allows appropriate water content for breeding the filamentous fungi to be maintained and the proliferation of the filamentous fungi and enzyme production by the filamentous fungi to be more activated. In addition, removal of the water included in the substrate after completion of the solid culture allows the deterioration of the substrate culture product or the feedstuff made by mixing the substrate culture product to be prevented and the quality to be stabilized. Consequently, the produced substrate culture product can be stored for a long period of time with the activity of the enzyme included in the substrate culture product maintained.

For example, the water content of the substrate culture product can be adjusted by the amount of water to be applied to the substrate in the raw material treatment process before inoculating on the substrate. The water content of the substrate when the inoculated substrate is placed in the solid culture apparatus (hereinafter, referred to as an initial water content) can be, for example, set to 30% by mass to 80% by mass and more, preferably set to 30% by mass to 55% by mass, or 56% by mass to 70% by mass. Here, the water content is a value obtained by allowing the substrate to stand for 15 hours in a dryer of 90° C. (absolute drying) and calculating from the weight before and after the drying.

The water content of the substrate culture product can be adjusted by, for example, after completion of the solid culture, ventilating the substrate with dry air to remove water contained in the substrate. The water content of the substrate when the solid-cultured substrate is taken out from the solid culture apparatus (hereinafter, referred to as a final water content) is, for example, preferably set to 25% by mass or less, and more preferably set to 14% by mass or less. The lower limit value of the water content of the substrate is not particularly limited. For example, the lower limit can be determined to be more than 0% by mass.

The substrate culture product preferably includes polysaccharides constituting the hyphae of the filamentous fungi. The cells constituting the hyphae are covered with cell walls. The main component of the cell wall is the polysaccharides. Examples of the polysaccharides include glucan, chitin, and chitosan. It is said that these polysaccharides are responsible for an immunity activating effect. Consequently, an effect of improving the immune strength of the animals ingesting the feedstuff is expected by including these polysaccharides in the substrate culture product. Proteins and lipids included in the fungi cells of the filamentous fungi are absorbed as nutrient contents of the animals ingesting the feedstuff.

The substrate culture product may be fed as it is, or may be mixed with other feedstuff and fed. The process of extracting the components including the target enzyme from the substrate culture product may be further carried out, and the extract may be fed to animals, or the extract may be mixed with other feedstuff and fed. The process of extracting the enzyme is preferably carried out using, for example, liquid such as a buffer solution or water. The enzyme may be taken out by immersing the substrate culture product into the liquid, physically grinding and liquefying the fungi cell by homogenizing or the like, and centrifuging or filtering the obtained liquid.

The substrate culture product produced by the above-described production method or the extract produced by the above-described production method may be used as feedstuff by carrying out a process of mixing the substrate culture product or the extract with a new substrate for which culture is not carried out. This allows a mixed feedstuff to be prepared by increasing the bulk of the substrate culture product or the extract and the degradation of the new substrate for which the culture is not carried out to be promoted. In the case where the viable fungi of the filamentous fungi are included in the substrate culture product, functionality may be imparted to the new substrate by mixing the new substrate and the substrate culture product and further culturing the mixture.

The feeding target of the substrate culture product used as the feedstuff is not particularly limited and examples of the feeding target include domestic animals such as cows, pigs, sheep, goats, and poultry; crustacea such as shrimps and crabs; or fish (including cultured fish). Examples of the poultry include chickens, ducks, domestic ducks, or geese. Ruminants such as cows, sheep, and goats have rumen bacteria in the first stomach called rumen. The rumen bacteria degrade the feedstuff to promote digestion. Production of a degrading enzyme that the rumen bacteria produce or a degrading enzyme acting together with the degrading enzyme that the rumen bacteria produce and exhibiting the synergistic effect in high productivity by the self-cloning results in exhibiting an effect to the digestion promotion for the ruminants.

EXAMPLES

Hereinafter, the present invention will be further specifically described with reference to Examples of the present invention. In Examples described below, genes coding phytase, polygalac-turonase, xylanase, or tannase were determined to be the targets of the self-cloning. Phytase was selected for the purpose of improving the absorption ratio of minerals by degrading phytic acid included in the feedstuff. Xylanase and polygalac-turonase were selected for the purpose of improving the digestion ratio of the feedstuff by degrading the polysaccharide constituting the cell walls of plants. Tannase was selected for the purpose of improving the digestion ratio of the feedstuff by degrading tannin bonded to the components constituting the cell walls of plants.

[Self-Cloning]

Using a koji mold genome database (www.aspgd.org/) and the database of glycosyl hydrolase CAZy (www.cazy.org/fam/acc_GH.html), genes coding phytase, polygalac-turonase, xylanase, or tannase were searched. With respect to phytase, phyA was determined to be a candidate gene. With respect to polygalac-turonase, pgaB was determined to be a candidate gene. With respect to xylanase, xynG1 was determined to be a candidate gene. With respect to tannase, tanA was determined to be a candidate gene. The DNA sequence of phyA is as listed in Sequence number 1 in SEQUENCE LISTING. The DNA sequence of pgaB is as listed in Sequence number 2 in SEQUENCE LISTING. The DNA sequence of xynG1 is as listed in Sequence number 3 in SEQUENCE LISTING. The DNA sequence of tanA is as listed in Sequence number 4 in SEQUENCE LISTING. The DNA sequence of amylase (AmyB) including the AmyB promoter and the AmyB terminator described below is listed in Sequence number 28 in SEQUENCE LISTING. The DNA sequence of enolase (enoA) including the enoA promoter and the enoA terminator described below is listed in Sequence number 29 in SEQUENCE LISTING.

Genetically transformed *Aspergillus oryzae* (hereinafter referred to a 2-4 strain) formed by self-cloning a total of two genes of the phyA gene and the pgaB gene and genetically transformed *Aspergillus oryzae* (hereinafter referred to a 3-12 strain) formed by self-cloning a total of three genes of the xynG1 gene, the phyA gene, and the tanA gene were prepared by the method described below. Hereinafter, the method will be described.

[Extraction of Genomic DNA]

The wild strain of the koji mold (*Aspergillus oryzae*, RIB40) issued from NBRC (National Institute of Technology and Evaluation) was liquid-cultured and a genomic DNA was extracted by the following method. Specifically, the conidia of the wild strain were inoculated in a liquid culture medium. To the fungi cells obtained by allowing to stand and culturing at 30° C. for 2 to 3 days, glass beads were added and the resultant mixture was vigorously stirred. Freeze-thawing was repeated to extract the genomic DNA. This wild strain is fungi not producing mold poison.

[Preparation of Gene Cassette]

Figure 3:
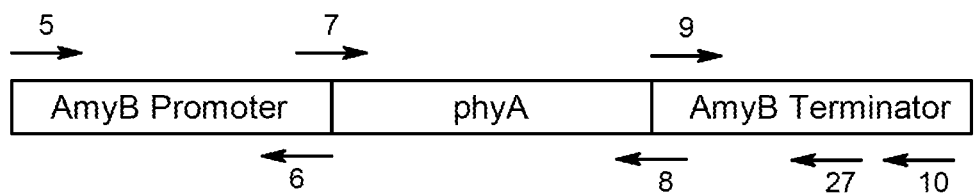
FIG. 3 is a view illustrating configurations of expression cassettes 1 to 5 and the positions of primers to be set.
Figure 3:
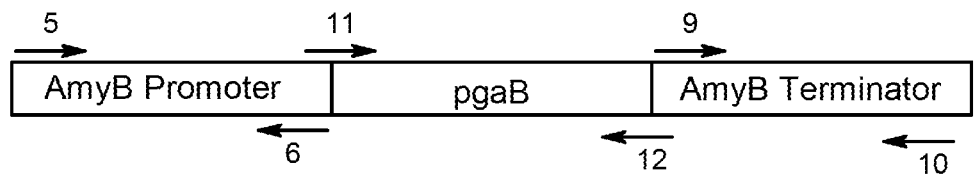
Figure 3:
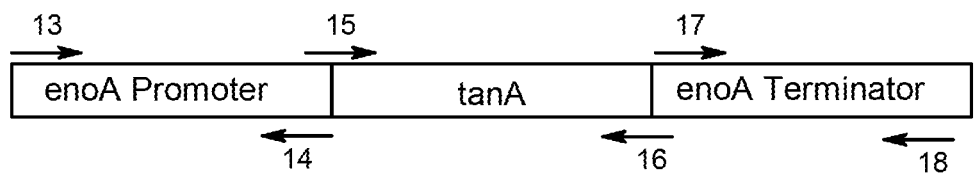
Figure 3:
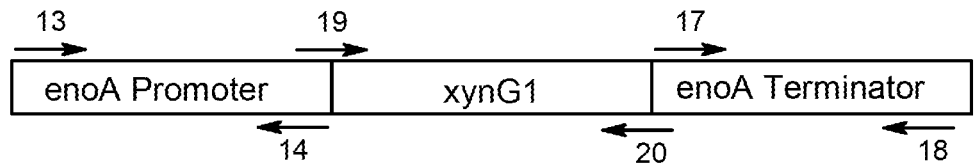
Figure 3:
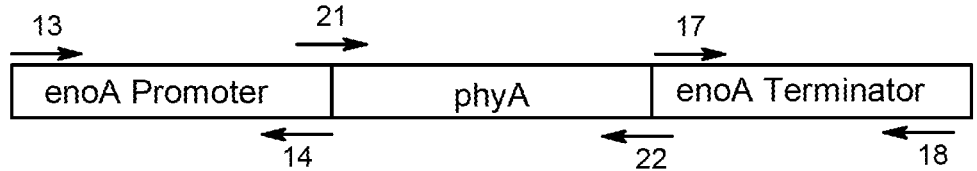

The genomic DNA extracted by the above-described method was used as a template to prepare expression cassettes 1 to 5 illustrated in FIG. 3. The expression cassette 1 or 2 has a base sequence in which each phyA or pgaB originated from the genomic gene of RIB40 is bonded as the target degrading enzyme between the amylase promoter (AmyB promoter) originated from the genomic gene of RIB40 and the amylase terminator (AmyB terminator) originated from the genomic gene of RIB40. The amylase promoter functions as a promoter for high expression.

The expression cassette 3, 4, or 5 has a base sequence in which each tanA, xynGl, or phyA originated from the genomic gene of RIB40 is bonded as the target degrading enzyme between the enolase promoter (enoA promoter) originated from the genomic gene of RIB40 and the enolase terminator (enoA terminator) originated from the genomic gene of RIB40. The enolase promoter functions as a promoter for high expression.

Each of the expression cassettes was synthesized by mixing the promoter sequence, the terminator sequence, and the gene of the degrading enzyme having a sequence overlapping to the promoter sequence at the 5'-terminal and having a sequence overlapping to the terminator sequence at the 3'-terminal and carrying out fusion PCR. The amplification and the fusion PCR of the promoter, terminator, and each degrading enzyme were carried out as follows.

[Amplification of Promoter Sequence and Terminator Sequence]

For the AmyB promoter, the AmyB promoter was amplified by setting a sense primer 5 and an antisense primer 6 illustrated in FIG. 3 and listed in SEQUENCE LISTING, and carrying out PCR in the following conditions. The sense primer 5 is illustrated by a reference sign 5 in FIG. 3 and the base sequence thereof is as listed in Sequence number 5 in SEQUENCE LISTING. The antisense primer 6 is illustrated by a reference sign 6 in FIG. 3 and the base sequence thereof is as listed in Sequence number 6 in SEQUENCE LISTING. As described above, in this specification, FIG. 3, FIG. 4, FIG. 5, and SEQUENCE LISTING, the reference sign illustrated in the drawings, the primer number described in this specification, and the sequence number in SEQUENCE LISTING shall be mutually matched with each other. For example, the base sequence of the sense primer 19 is determined to be the sequence listed in Sequence number 19 in SEQUENCE LISTING. The sequence number is listed as <210> in SEQUENCE LISTING. Hereinafter, the same will apply.

(Composition of PCR Reaction Liquid)

| Template (RIB40 genomic DNA) | 1 μl |
|---|---|
| 10 mM dNTP | 1 μl |
| 5 × Q5 buffer solution | 10 μl |
| 50 μM Sense primer 5 | 0.5 μl |
| 50 μM Antisense primer 6 | 0.5 μl |
| DNA polymerase (Q5) | 0.5 μl |
| Distilled water | 36.5 μl |

(Conditions of PCR Reaction)

1. 98° C. for 30 seconds
2. 30 times of cycles (98° C. for 10 seconds to 72° C. for 30 seconds)
3. 72° C. for 5 minutes
4. Maintaining at 12° C.

For the AmyB terminator, the AmyB terminator was amplified by the same conditions as conditions for the AmyB promoter except that a sense primer 9 and an antisense primer 10 illustrated in FIG. 3 and listed in SEQUENCE LISTING were set. Similarly, for the enoA promoter, the enoA promoter was also amplified by the same conditions as conditions for the AmyB promoter except that a sense primer 13 and an antisense primer 14 illustrated in FIG. 3 and listed in SEQUENCE LISTING were set. Similarly, for the enoA terminator, the enoA terminator was also amplified by the same conditions as conditions for the AmyB promoter except that a sense primer 17 and an antisense primer 18 illustrated in FIG. 3 and listed in SEQUENCE LISTING were set.

[Amplification of Target Degrading Enzyme Gene]

For the phyA gene used in the expression cassette 1, the phyA gene was amplified by setting a sense primer 7 and an antisense primer 8 illustrated in FIG. 3 and listed in SEQUENCE LISTING and carrying out PCR in the following conditions.

(Composition of PCR Reaction Liquid)

| Template (RIB40 genomic DNA) | 1 μl |
|---|---|
| 10 mM dNTP | 1 μl |
| 5 × Q5 buffer solution | 10 μl |
| 50 μM Sense primer 7 | 0.5 μl |
| 50 μM Antisense primer 8 | 0.5 μl |
| DNA polymerase (Q5) | 0.5 μl |
| Distilled water | 36.5 μl |

(Conditions of PCR Reaction)

1. 98° C. for 30 seconds
2. 30 times of cycles (98° C. for 10 seconds to 72° C. for 1 minute)
3. 72° C. for 5 minutes
4. Maintaining at 12° C.

For pgaB, pgaB was also amplified by the same conditions as conditions for the case of phyA except that a sense primer 11 and an antisense primer 12 illustrated in FIG. 3 and listed in SEQUENCE LISTING were set. Similarly, for phyA used in the expression cassette 5, phyA for the expression cassette 5 was also amplified by the same conditions as conditions for the case of phyA except that a sense primer 21 and an antisense primer 22 illustrated in FIG. 3 and listed in SEQUENCE LISTING were set. Similarly, for xynG1, xynG1 was also amplified by the same conditions as conditions for the case of phyA except that a sense primer 19 and an antisense primer 20 illustrated in FIG. 3 and listed in SEQUENCE LISTING were set.

For the tanA gene, the tanA gene was amplified by setting a sense primer 15 and an antisense primer 16 illustrated in FIG. 3 and listed in SEQUENCE LISTING and carrying out PCR in the following conditions.

(Composition of PCR Reaction Liquid)

| Template (RIB40 genomic DNA) | 1 μl |
|---|---|
| 10 mM dNTP | 2 μl |
| 2 × KOD buffer solution | 25 μl |
| 50 μM Sense primer 15 | 0.2 μl |
| 50 μM Antisense primer 16 | 0.2 μl |
| DNA polymerase (KOD Fx neo) | 1 μl |
| Distilled water | 20.6 μl |

(Conditions of PCR Reaction)

1. 94° C. for 2 minutes
2. 40 times of cycles (from 98° C. for 10 seconds, through 58° C. for 30 seconds, to 68° C. for 1 minute 15 seconds)
3. 68° C. for 5 minutes
4. Maintaining at 12° C.

[Fusion PCR]

For the expression cassette 1 illustrated in FIG. 3, the phyA gene was amplified by using the above-described sense primer 5 and an antisense primer 27 illustrated in FIG. 3 and listed in SEQUENCE LISTING and carrying out PCR in the following conditions. Here, KOD Fx neo (manufactured by TOYOBO CO., LTD.) is a commercially available DNA polymerase.

(Composition of PCR Reaction Liquid)

| Template (AmyB promoter) | 1 μl |
|---|---|
| Template (AmyB terminator) | 1 μl |
| Template (phyA for expression cassette 1) | 1 μl |
| 10 mM dNTP | 2 μl |
| 2 × KOD buffer solution | 25 μl |
| 50 μM Sense primer 5 | 0.2 μl |
| 50 μM Antisense primer 27 | 0.2 μl |

| | |
|---|---|
| DNA polymerase (KOD Fx neo) | 1 μl |
| Distilled water | 18.6 μl |

(Conditions of PCR Reaction)
 1. 94° C. for 2 minutes
 2. 40 times of cycles (from 98° C. for 10 seconds, through 58° C. for 30 seconds, to 68° C. for 2 minutes)
 3. 68° C. for 5 minutes
 4. Maintaining at 12° C.

For the expression cassette 2 illustrated in FIG. 3, the expression cassette 2 was amplified by carrying out PCR with the same conditions as conditions for the case of the expression cassette 1 except that pgaB synthesized by the above-described method was used instead of phyA for the expression cassette 1.

For the expression cassette 3 illustrated in FIG. 3, the expression cassette 3 was amplified by carrying out PCR with the same conditions as conditions for the case of the expression cassette 2 except that tanA synthesized by the above-described method was used instead of phyA for the expression cassette 1, the enoA promoter amplified by the above-described method was used instead of the AmyB promoter, the enoA terminator amplified by the above-described method was used instead of the AmyB terminator, a sense primer 13 was used instead of the sense primer 5, and an antisense primer 18 was used instead of the antisense primer 27. For the expression cassette 4 illustrated in FIG. 3, the expression cassette 4 was amplified by carrying out PCR with the same conditions as conditions for the case of the expression cassette 3 except that xynG1 synthesized by the above-described method was used instead of tanA. For the expression cassette 5 illustrated in FIG. 3, the expression cassette 5 was amplified by carrying out PCR with the same conditions as conditions for the case of the expression cassette 4 except that phyA for the expression cassette 5 synthesized by the above-described method was used instead of xynG1 for the expression cassette 4.

[Preparation of 2-4 Strain]

Figure 4:
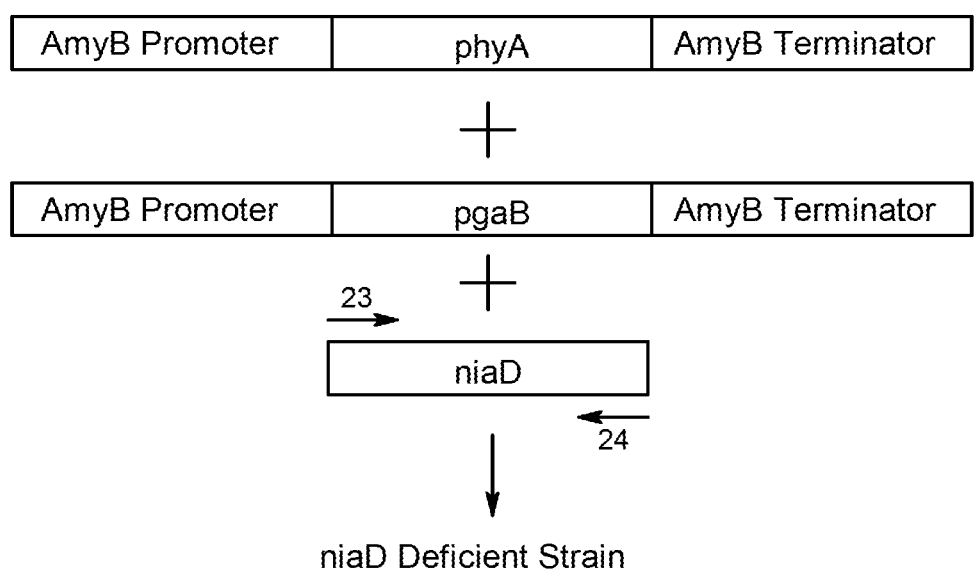
FIG. 4 is a view illustrating expression cassettes introduced when a 2-4 strain is prepared, marker genes, and positions of primers to be set.

A niaD deficient strain was selected from *Aspergillus oryzae* (AOK11) commercially available as a koji mold for sake brewing by the method described in Mon Gen Genet (1989) 218:99-104. This deficient strain is fungi not producing mold poison. To the niaD deficient strain, the expression cassette 1, the expression cassette 2, and the niaD gene prepared by the above methods were co-transformed as illustrated in FIG. 4.

The niaD gene was amplified by setting a sense primer 23 and an antisense primer 24 illustrated in FIG. 4 and listed in SEQUENCE LISTING and carrying out PCR in the following conditions. Here, Q5 (manufactured by New England Biolabs Japan Inc.) is a commercially available DNA polymerase.

(Composition of PCR Reaction Liquid)

| | |
|---|---|
| Template (RIB40 genomic DNA) | 2 μl |
| 10 mM dNTP | 1 μl |
| 5 × Q5 buffer solution | 10 μl |
| 50 μM Sense primer 23 | 0.5 μl |
| 50 μM Antisense primer 24 | 0.5 μl |
| DNA polymerase (Q5) | 0.5 μl |
| Distilled water | 35.5 μl |

(Conditions of PCR Reaction)
 1. 98° C. for 30 seconds
 2. 30 times of cycles (98° C. for 10 seconds to 72° C. for 2 minutes 30 seconds)
 3. 72° C. for 5 minutes
 4. Maintaining at 12° C.

The co-transformation of the cassette 1, the cassette 2, and niaD was carried out by a protoplast-PEG method. About 1×10$^6$ conidia of the host strain were inoculated in 50 ml of a liquid culture medium to culture at 120 rpm and 30° C. for 36 hours. The fungi cells were recovered using a sterilized glass filter and suspended in protoplasted solution that was filtered and sterilized. To the protoplast recovered by shaking the suspended mixture at 120 rpm and 30° C. for 2 to 3 hours to react and thereafter filtering the reacted mixture with Miracloth, the expression cassette 1, the expression cassette 2, and the niaD gene (a genetic transformation marker) were added and the resultant mixture was sufficiently mixed. Protoplast fusion was promoted in a solution containing 40% (w/v) PEG 6000 and 50 mM $CaCl_2$ to introduce each DNA into cells.

Selection of the transformant using the niaD marker was carried out by selecting a strain that can grow in minimum culture medium in which 0.6% $NaNO_3$ was used as a nitrogen source. For the selected strain, PCR was carried out using the sense primer 7 and the antisense primer 10, and the sense primer 11 and the antisense primer 10 to selected a strain into which both of the phyA gene and pgaB gene were introduced.

[Preparation of 3-12 Strain]

Figure 5:
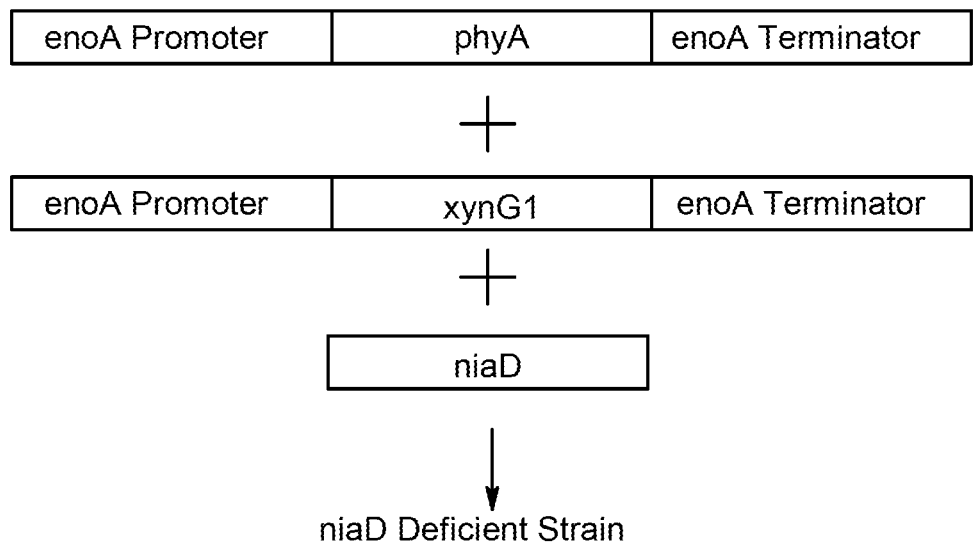
FIG. 5 is a view illustrating expression cassettes introduced when a 3-12 strain is prepared, marker genes, and positions of primers to be set.
Figure 5:
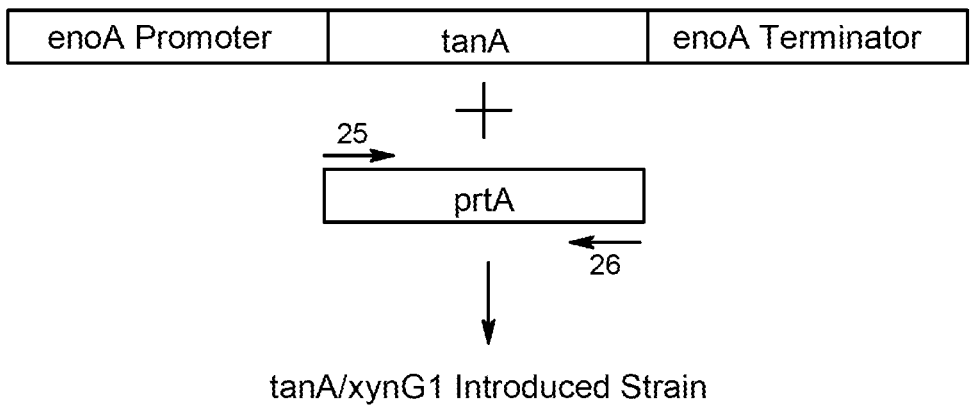

As illustrated in FIG. 5, a transformant into which both of the phyA gene and xynG1 gene were introduced in the same method as the preparation method of the 2-4 strain except that the expression cassette 4 and the expression cassette 5 were used instead of the expression cassette 1 and the expression cassette 2.

With respect to the trasformant into which the phyA gene and the xynG1 gene were introduced that is explained above, the expression cassette 3 and a prtA gene (a selection marker) were co-transformed by the same method as the method described above.

The prt gene was amplified by setting a sense primer 25 and an antisense primer 26 illustrated in FIG. 5 and listed in SEQUENCE LISTING and carrying out PCR in the following conditions. Here, pPTRI (manufactured by TAKARA Bio Inc.) used as a template is a commercially available vector used in the cloning of the koji mold.

(Composition of PCR Reaction Liquid)

| | |
|---|---|
| Template (pPTRI) | 2 μl |
| 10 mM dNTP | 1 μl |
| 5 × Q5 buffer solution | 10 μl |
| 50 μM Sense primer 25 | 0.5 μl |
| 50 μM Antisense primer 26 | 0.5 μl |
| DNA polymerase (Q5) | 0.5 μl |
| Distilled water | 35.5 μl |

(Conditions of PCR Reaction)
 1. 98° C. for 30 seconds
 2. 30 times of cycles (98° C. for 10 seconds to 72° C. for 1 minute)
 3. 72° C. for 5 minutes
 4. Maintaining at 12° C.

As the selection of a transformant using the prtA marker, the transformant was selected by adding pyrithiamine to the minimum culture medium in which 0.6% $NaNO_3$ was used as a nitrogen source. PCR was carried out using the sense primer 15 and the antisense primer 18, the sense primer 19 and the antisense primer 18, and the sense primer 21 and the antisense primer 18 to select a strain into which tanA, xynG1, and phyA were introduced.

[Culture Conditions]

Each of the seed fungi of the AOK11 wild strain (hereinafter, referred to as a "wild strain") or the 2-4 strain or the 3-12 strain bred by the self-cloning was inoculated on bran serving as a substrate to carry out the solid culture. Specific culture conditions are as follows.

(1) Culture of Wild Strain: Initial Water Content 60%, Base Pattern

To 160 kg of bran having a water content of 11%, water was added so as to be a water content of 58% and stirred. Thereafter, the water-added bran was treated by steaming under pressure at 0.2 MPa. After completion of the steaming treatment under pressure, the bran was cooled to about 30° C. The seed fungi of the AOK11 wild strain were inoculated at a certain amount and the inoculated bran was carefully mixed so as to be uniform. The water content of the raw material after inoculating was 60%. This raw material was placed on the culture bed in the culture apparatus and smoothed so that the layer thickness was constant. Thereafter, the culture was started. During the culture, the substrate was ventilated with air in which temperature and humidity were strictly controlled to control the substance temperature so as to be the substance temperature process of the base pattern. The substance temperature process of the base pattern is listed in Table 1. Here, in the base pattern, a period after a culture time of 21 hours corresponds to the enzyme production period.

TABLE 1

| Culture time (h) | | 0-9 | 6-12 | 12-18 | 18-21 | 21-24 | 24-27 | 27-60 |
|---|---|---|---|---|---|---|---|---|
| Temperature (° C.) | Base pattern | 28 | 32 | 35 | 38 | | 37 | |
| | Low temperature pattern | | | | | 35 | 33 | 32 |

(2) Culture of 2-4 Strain: Initial Water Content 60%, Base Pattern

To 160 kg of bran having a water content of 11%, water was added so as to be a water content of 58% and stirred. Thereafter, the water-added bran was treated by steaming under pressure at 0.2 MPa. After completion of the steaming treatment under pressure, the bran was cooled to about 30° C. The seed fungi of the 2-4 strain were inoculated at a certain amount and the inoculated bran was carefully mixed so as to be uniform. The water content of the raw material after inoculating was 60%. This raw material was placed on the culture bed in the culture apparatus and smoothed so that the layer thickness was constant. Thereafter, the culture was started. During the culture, the substrate was ventilated with air in which temperature and humidity were strictly controlled to control the substance temperature so as to be the substance temperature process of the base pattern.

(3) Culture of 2-4 Strain: Initial Water Content 50%, Base Pattern

To 160 kg of bran having a water content of 11%, water was added so as to be a water content of 48% and stirred. Thereafter, the water-added bran was treated by steaming under pressure at 0.2 MPa. After completion of the steaming treatment under pressure, the bran was cooled to about 30° C. The seed fungi of the 2-4 strain were inoculated at a certain amount and the inoculated bran was carefully mixed so as to be uniform. The water content of the raw material after inoculating was 50%. This raw material was placed on the culture bed in the culture apparatus and smoothed so that the layer thickness was constant. Thereafter, the culture was started. During the culture, the substrate was ventilated with air in which temperature and humidity were strictly controlled to control the substance temperature so as to be the substance temperature process of the base pattern.

(4) Culture of 3-12 Strain: Initial Water Content 60%, Base Pattern

To 160 kg of bran having a water content of 11%, water was added so as to be a water content of 58% and stirred. Thereafter, the water-added bran was treated by steaming under pressure at 0.2 MPa. After completion of the steaming treatment under pressure, the bran was cooled to about 30° C. The seed fungi of the 3-12 strain were inoculated at a certain amount and the inoculated bran was carefully mixed. The water content of the raw material after inoculating was 60%. This raw material was placed on the culture bed of a culture apparatus and smoothed so that the layer thickness was constant. Thereafter, the culture was started. During the culture, the substrate was ventilated with air in which temperature and humidity were strictly controlled to control the substance temperature so as to be substance temperature process of the base pattern.

(5) Culture of 3-12 Strain: Initial Water Content 50%, Base Pattern

To 160 kg of bran having a water content of 11%, water was added so as to be a water content of 48% and stirred. Thereafter, the water-added bran was treated by steaming under pressure at 0.2 MPa. After completion of the steaming treatment under pressure, the bran was cooled to about 30° C. The seed fungi of the 3-12 strain were inoculated at a certain amount and the inoculated bran was carefully mixed. The water content of the raw material after inoculating was 50%. This raw material was placed on the culture bed of a culture apparatus and smoothed so that the layer thickness was constant. Thereafter, the culture was started. During the culture, the substrate was ventilated with air in which temperature and humidity were strictly controlled to control the substance temperature so as to be substance temperature process of the base pattern.

(6) Culture of 3-12 Strain: Initial Water Content 60%, Low Temperature Pattern

To 160 kg of bran having a water content of 11%, water was added so as to be a water content of 58% and stirred. Thereafter, the water-added bran was treated by steaming under pressure at 0.2 MPa. After completion of the steaming treatment under pressure, the bran was cooled to about 30° C. The seed fungi of the 3-12 strain were inoculated at a certain amount and the inoculated bran was carefully mixed so as to be uniform. The water content of the raw material after inoculating was 60%. This raw material was placed on the culture bed in the culture apparatus and smoothed so that the layer thickness was constant. Thereafter, the culture was started. During the culture, the substrate was ventilated with air in which temperature and humidity were strictly controlled to control the substance temperature so as to be the substance temperature process of the low temperature pattern. The substance temperature process of the low temperature pattern is listed in Table 1. Here, in the low temperature pattern, a period after a culture time of 27 hours corresponds to the enzyme production period.

[Evaluation of Enzyme Activity]

The activity of the enzymes contained in the substrate culture product of (1) to (6) was evaluated. The extraction of crude enzyme liquid from each of the substrate culture products and the measurement of the activity of each of the enzymes were carried out by known methods. In the enzyme activity evaluation, the activity of each of the enzymes in (1) was used as a control and the enzyme activity was evaluated by the corresponding magnification of the activity of each of the enzymes in (2) to (6) to the control.

Evaluation of Phytase Activity and Polygalac-Turonase Activity in 2-4 Strain

The activities of phytase contained in the substrate culture products in (2) and (3) were 9 times to 17 times as compared to the control. The activities of polygalac-turonase contained in the substrate culture products in (2) and (3) were 14 times to 15 times as compared to the control. From these results, it is confirmed that in the 2-4 strain to breed two kinds of the degrading enzyme, phytase and polygalac-turonase, in high expression, the target degrading enzymes were produced by the self-cloning in high productivity.

Evaluation of Tannase Activity, Xylanase Activity, and Phytase Activity in 3-12 Strain The activities of tannase contained in the substrate culture products in (4), (5), and (6) were 2 times to 4 times as compared to the control. The activities of xylanase contained in the substrate culture products in (4), (5), and (6) were 21 times to 43 times as compared to the control. The activities of phytase contained in the substrate culture product in (4), (5), and (6) were 11 times to 18 times as compared to the control. From these results, it is confirmed that in the 3-12 strain to breed three kinds of the degrading enzyme, tannase, xylanase, and phytase, in high expression, the target degrading enzymes were produced by the self-cloning in high productivity.

[Evaluation of Digestion Ratio by Artificial Rumen Method]

The digestion ratio was evaluated by the artificial rumen method using a digestion test apparatus (ANKOM DAISY II in vitro incubator). First, into a glass bottle (digestion jar) serving as a constitution parts of the digestion test apparatus, 400 mL of a liquid in which rumen juice collected from the first stomach of a cow was diluted four times and 1,600 mL of artificial saliva of a cow were charged and the resultant mixed liquid was sufficiently mixed to use as a reaction liquid. Subsequently, about 0.4 g of each soybean lees or rapeseed lees was placed in a mesh bag made of polyester and the mesh bag was sealed. Ten mesh bags containing soybean lees and ten mesh bags containing rapeseed lees were immersed into the reaction liquid. One gram of one kind of the substrate culture products (1) to (6) was added thereto and carbon dioxide gas was filled and sealed. Thereafter, the reaction was carried out in the digestion test apparatus maintaining at 39° C. for 48 hours. When 24 hours had passed and 48 hours had passed, each group of 5 mesh bags described above was taken out, sufficiently washed with flowing water, and allowed to stand for 15 hours in the dryer of 90° C. (absolute drying). Thereafter, the weight of each of the mesh bags was measured. The digestion ratios of the soybean lees and rapeseed lees were calculated from the weight change before and after the reaction. Here, a sample formed by adding 1 g of the substrate (bran) before the solid culture into the digestion jar where the reaction liquid and the mesh bags were placed was used as a control.

Hereinafter, the results of the artificial rumen test will be described for each of the reaction conditions.

In the Case Where the Wild Strain, the 2-4 Strain, and the 3-12 Strain were Cultured in Same Substance Temperature Pattern and the Same Initial Water Content Compared to an experimental section in which the substance temperature pattern was determined to be the base pattern and the substrate culture product (the substrate culture product in (1)) of the wild strain cultured at an initial water content of 60% was added, an experimental section in which the substrate culture product (the substrate culture product in (2)) of the 2-4 strain cultured in the same substance temperature pattern and the same initial water content was added had the digestion ratio of the soybean lees that is 9.9% higher at maximum and the digestion ratio of the rapeseed lees that is 10.5% higher at maximum. Compared to an experimental section in which the substance temperature pattern was determined to be the base pattern and the substrate culture product (the substrate culture product in (1)) of the wild strain cultured at an initial water content of 60% was added, an experimental section in which the substrate culture product (the substrate culture product in (4)) of the 3-12 strain cultured in the same substance temperature pattern and the same initial water content was added had the digestion ratio of the soybean lees that is 13.1% higher at maximum and the digestion ratio of the rapeseed lees that is 14.7% higher at maximum.

From the above-described results, it was found that, for the wild strain, the 2-4 strain, and the 3-12 strain evaluated this time, in the case where these strains were cultured in the same substance temperature pattern and the same initial water content, the solid-cultured 2-4 strain and 3-12 strain provided the substrate culture product having more efficiency for the digestion of the soybean lees and the rapeseed lees than the efficiency provided by the solid-cultured wild strain. Subsequently, for the 2-4 strain and the 3-12 strain, effect of the initial water content in the case of culturing in accordance with the base pattern was evaluated.

In the Case Where the 2-4 Strain was Cultured in Same Substance Temperature Pattern and the Water Content Varied Compared to an experimental section in which the substrate culture product (the substrate culture product in (3)) having an initial water content of 50% was added, an experimental section in which the substrate culture product (the substrate culture product in (2)) having an initial water content of 60% was added had the digestion ratio of the soybean lees that is 1.6% to 8.2% higher at maximum and the digestion ratio of the rapeseed lees that is 3.5% to 5.1% higher at maximum.

In the Case where the 3-12 Strain was Cultured in Same Substance Temperature Pattern and the Water Content Varied Compared to an experimental section in which the substrate culture product (the substrate culture product in (5)) having an initial water content of 50% was added, an experimental section in which the substrate culture product (the substrate culture product in (4)) having an initial water content of 60% was added had the digestion ratio of the soybean lees that is 1.9% to 5.5% higher at maximum and the digestion ratio of the rapeseed lees that is 2.2% to 4.0% higher at maximum.

From the above-described results, it was found that, for the 2-4 strain and the 3-12 strain evaluated this time, the solid culture products having an initial water content of 60% provided the substrate culture product having more efficient for the digestion of the soybean lees and the rapeseed lees. Therefore, for the 3-12 strain, the effect of the substance temperature pattern in the case of culturing at an initial water content of 60% was evaluated.

In the Case Where the 3-12 strain was Cultured in Same Initial Water Content and the Substance Temperature Pattern Varied Compared to an experimental section in which the substrate culture product (the substrate culture product in (4)) cultured according to the base pattern was added, an experimental section in which the substrate culture product (the substrate culture product in (6)) cultured in accordance with the low temperature pattern was added had the digestion ratio of the soybean lees that is 1.0% higher at maximum and the digestion ratio of the rapeseed lees that is 0.8% higher at maximum.

From the above-described results, it was found that, for the 3-12 strain evaluated this time, the substrate culture product solid-cultured in accordance with the low temperature pattern provided the substrate culture product having more efficiency for the digestion of the soybean lees and the rapeseed lees. In the above-described Examples, the digestion ratio of the soybean lees and the rapeseed lees were evaluated by the artificial rumen method. The improvement of the digestion ratios of other feedstuffs such as the squeezed lees of sesame and the squeezed lees of corn were also confirmed. When strains other than the strains evaluated in Examples such as a strain highly expressing three enzymes such as phytase (phyA), xylanase (xynG1), and pectin lyase (pelA) and a strain highly expressing four enzymes such as phytase (phyA), polygalac-turonase (pgaB), tannase (tanA), and pectin lyase (pelA) were solid-cultured, the substrate culture products effective for the digestion of the soybean lees and the rapeseed lees in the artificial rumen method were obtained. From the above results, it has been clear that feeding the substrate culture product produced by the method according to the present invention to animals as the feedstuff improves the digestion ratio of the feedstuff by the action of the degrading enzymes. The substrate culture product further includes the polysaccharides that constitute the hyphae of the filamentous fungi and thus improvement in the immune strength of animals ingesting the substrate culture product is expected.

Reference to a "Sequence Listing," a Table, or a Computer Program Listing Appendix Submitted as an ASCII Text File The material in the ASCII text file, named "MORI-61557-Sequence-Listing_ST25.txt", created Sep. 26, 2019, file size of 32,768 bytes, is hereby incorporated by reference.

The invention claimed is:

1. A method for producing a culture product used for feedstuff, the method comprising:
   inoculating a filamentous fungi on a solid substrate,
   wherein said filamentous fungi expresses an increased amount of an exogenous target degrading enzyme compared to a non-modified filamentous fungi, and
   wherein said exogenous target enzyme is a target enzyme from the same species of said filamentous fungi;
   culturing said filamentous fungi on said solid substrate; and
   ventilating by supplying external air to produce the culture product;
   wherein said culture product is in a solid-form which includes the target degrading enzyme.

2. The method for producing a culture product according to claim 1, wherein the filamentous fungi are fungi not producing mold poison.

3. The method for producing a culture product according to claim 2, wherein the fungi not producing mold poison are *Aspergillus oryzae, Aspergillus sojae,* or *Aspergillus luchuensis.*

4. The method for producing a culture product according to claim 1, wherein the solid culture is carried out by controlling temperature of the substrate by adjusting at least one of temperature and humidity of the external air supplied to the substrate.

5. The method for producing a culture product according to claim 1, wherein a water content of the culture product is adjusted by sprinkling water or drying, the adjustment of the water content is conducted during the solid culture or after the completion of the solid culture.

6. The method for producing a culture product according to claim 1, wherein the culture product includes polysaccharides constituting hyphae of the filamentous fungi.

7. The method for producing a culture product according to claim 1, further comprising mixing the produced culture product and a new substrate for which culture is not carried out.

8. The method for producing a culture product according to claim 1, wherein the filamentous fungi is a recombinant that is introduced with at least two genes that encode the degrading enzyme.

9. The method for producing a culture product according to claim 1, wherein the degrading enzyme includes one or more enzymes selected from the group consisting of amylase, alkaline protease, acidic protease, neutral protease, xylanase, β-glucanase, cellulase, tannase, phytase, lactase, lipase, and pectinase.

10. The method for producing a culture product according to claim 1, further comprising carrying out co-transformation, into the filamentous fungi, a target degrading enzyme gene, a promoter sequence, and a terminator sequence from the species from which the incorporated gene sequence is obtained.

11. The method for producing a culture product according to claim 1, further comprising adding the culture product to a feed to make a feedstuff.

12. The method for producing a culture product according to claim 11, wherein the culture product improves a digestion ratio of the feedstuff compared to a feedstuff lacking the degrading enzyme or compared to a feedstuff not prepared by the same method.

* * * * *

SEQUENCE LISTING

```
<160> NUMBER OF SEQ ID NOS: 29

<210> SEQ ID NO 1
<211> LENGTH: 3559
<212> TYPE: DNA
<213> ORGANISM: Aspergillus oryzae

<400> SEQUENCE: 1
gcaaaacggg aaaaaggagc gaaagcacag aaatgaagaa aaaatgaaag aaaagaaaaa      60
aacaaggcaa tgtcaacaac cgttgtggat ctctgtcgga ctctccgaca accgacgatg     120
atcgttatca aatgagatgc acgggtagag atgatcagat gcggccccca gcaccacaac     180
gagattttat taggtcatta gattgtttta ctgaagcatt aaagcattgt cattttgtct     240
ggtgcgtttt cccgacgatt ccagtctttg ttgacggcca tgtgaatctt gtagctctcc     300
gtgaggtttc cacatcttga cttggaatat acgggttgtc ccgagactaa ggaagggcga     360
atattagaag agagagagag agaaaaaaaa attcgacagg aaaaagagga aagaaaaaag     420
gatattacat aaataaccat ctttaaccag acttcgaagg aatattcgcg caaagcgtgg     480
gaagtgtatt ggctgtagtt gactgattga taacccgtgg ctgatcaata tcaaaccggc     540
taaagcaacg gcttcccgct cgttagaagt ggatcattgc gaccgtcgcc ttgtacgagt     600
tgatcaagct tgaaccacag atcttaactt caattgaata gaagtccgac cggattccga     660
agggatgtct aggattatgg aaccctgcgt ctcccttct tttccttcag gcacacttgt      720
caccattccc gcgaccacgt gggcccaaca cagcctatca gcgtcacaga gacaactcac     780
gttatcctcg acgtttctct ctcgtatatt ctccccatc agcacctcct aagaaccatg      840
ggtgatcgga caccatgtct tacactgcag gcttatcctc tttcaccccc actacactac     900
cgcttcacta gcaccacggc tgaatctccg tccgatatcg cgggatcgta agctgcgcta     960
gggttacaag gtctccggtt gggatcaaca tgagacggaa atgaagggct tatatgagga    1020
ccgtcccgtc cgcgtggagg ggttgttccg tcgtttgtct aacagtaaaa gggttgcaat    1080
cgtgagcatc atggcggtcc ttagcgtgct ccttcccatt accttccttc tctcgaggta    1140
```

```
agctcaccca tagatgctgc cctatagtgg atgccctaat ctaacagcgg ctgatcttca    1200
ttcagtgtta ccggcactcc ggtgaccagc ccgagacaac agtcgtgcaa taccgttgac    1260
gaaggctacc agtgcttctc cggggtctct cacttgtggg gccagtattc gccttacttc    1320
tcggtcgacg acgagtcttc cttgtccgaa gacgttccgg accactgcca ggttaccttt    1380
gcccaagtgc tctcccgtca cggtgcacgg tatccaacga agagcaagtc tgagaagtac    1440
gccaagctca tcaaggccgt ccagcataat gctacctcgt tctccgggaa gtatgcgttc    1500
ctgaaatctt acaactactc cctcggcgcc gatgacctta cgccttttgg agagaaccag    1560
ttggtggatt cggggatcaa gttctaccag cgctatgagg agctcgccaa gaacgtcgtt    1620
cctttcatta gggcatcggg ttcggatcgg gtaatcgcat ccggcgagaa attcatcgag    1680
ggcttccaga aggcaaagct tggtgactct aagtctaagc ggggccagcc tgctcctatt    1740
gtcaacgtag ttattactga gaccgagggt ttcaacaaca cgttggacca cagtctctgc    1800
acggcctttg agaacagcac aacagggat gacgcagagg acaagttcac cgctgttttt    1860
acgccctcga ttgttgagcg tctggagaag gacctcccag gaaccacgct ctccagcaaa    1920
gaggtggttt atctgatgga catgtgctca ttcgacacca tcgccttgac ccgtgacggc    1980
agtcggctat cccccttctg cgctttgttc acccaggaag aatgggcaca atatgactac    2040
ctgcagtcag tctctaagta ctacggctac ggtggaggaa accctctcgg acctgcgcag    2100
ggcatcggct tcgctaacga gctgatcgct cgcctgacca agtctccggt taaggatcac    2160
accaccacca ataccacgct ggactcaaat cccgccacct tcccgctgaa tgctacgctc    2220
tatgcggact tctcgcacga taacacgatg acctccgttt tcttcgcgct tggtctgtat    2280
aatacgaccg agcccctctc tcagacttcg gtgcagtcca ctgaggagac gaacggatat    2340
tcatccgccc ggaccgttcc attcggggcc agagcctacg tcgagatgat gcagtgcacg    2400
gatgagaagg agcctctcgt ccgcgtactg gtcaacgacc gggtcattcc gctgcaaggc    2460
tgtgatgctg atgagtatgg ccggtgtaaa cgggacgatt tcgtcgaagg actgagcttc    2520
gttacatcgg gtggaaactg gggagagtgc tttgcttaag ctggggatat actcaagttg    2580
tcaccgctct actctttctg tctttctttc agactttctt cattcataca aggcaactta    2640
atacacaaaa ctgtacacaa agagcagcga tacccactca ataaaaagca atatcattgc    2700
atcttcatcg agatcacaat cacagctata gacactcatc cttagacatc atactccctc    2760
catcatctac aacatgttct acacaatcct cgcatgaaaa agtaaaagca cacatctcct    2820
tacccccaga aacatctcaa cgagcaccat accaaaccaa acaaagtggt cttaaacaac    2880
aacctacacc atactaacac aaaccagctc tatacaaata caacctgacc ctacaacaaa    2940
cacatcccaa ccaagaaaac atttcatgaa taccccaatc ccacaaacta atatacaatt    3000
aaaccagaca agaaaaagcc atcccccaaa actactaaat caagcactcc catccttcct    3060
ctcctcagtc ccagaccctg acggccgagc caaatgcttc tggctcttgt tcaaataagc    3120
taaacaacca gatcagcact cctttaccca gtcccaaaca aaacaagga ttaaaagaac    3180 aaaaaaaaaa agaattgaat gaagaacaag aaaaagaaaa aagaactcac tcctctcata    3240
aagcacataa gaagtataca tcaaaatagg caacgccacg atcgttgaaa gccatctatc    3300
acattgtcaa tatcagatga tctccaattc aacacgagca tagttaatgg tcaatccgag    3360
tccacaaact cgcccatatc ttcatcttga gataaataag gaaatataaa tataagaaac    3420
ataccgtcta gcagcaattt tatattcctt cgtttgccga atatcccgta cactttgtgg    3480
```

```
accgcgccgg ggtggatggg gtggtcgttg aagggattgc gggttgatga ttacgcgggg   3540
ttgttggttg gacattttt                                                3559

<210> SEQ ID NO 2
<211> LENGTH: 3226
<212> TYPE: DNA
<213> ORGANISM: Aspergillus oryzae

<400> SEQUENCE: 2
gaatcaattg tccgacgata tcgaggacat ttcatcaatc cagaacacca caatacttgg     60
ttagagaatg atgtcacgat cccttttgtga ggtgtcaaag cgccaggctg atccggagat   120
ttgccgaata tgacaaatcc gtattggtga ttctgaccgt tgatccctct ctattttctg    180
gaaaaagatg agacccctca ttcagggatt tcaggcaacc caatttaggg tagattaaac    240
cgacaagtta aggctcaaaa tggataaatc catgatgccg ggtaatccgt accttcggtc    300
ccagccaacg ggatatcaca aatcaccctg gcttgaaacc acgacgaata ggcagcaccg    360
gagaataaac ggcaaaacct tttagtgagc tagcgaactt taccagagga accatgtggg    420
ctagctcctt tccgatgtac cgaaaggacc acgatgcccg atgcccactg gcacaagtag    480
ggacctagct ccctcagagt gagacaagca tgagacaaag ggtgggatat gggcgaggga    540
gttcggcaga tgagcaccta ttatcccgat tgttggacga aagatgaact gaggactgac    600
ggtggggccg agccttaccg gatcttggct tgaaccccta gggcccatgg gtccgctatg    660
ccctaaacgc ctcctagggc tgcgctcgtc gttagaggtt gatgatactg ataatagcac    720
ggtggaacag tctcgtagtg gagattttcg ttccaccaat aactgaatta tttcggtatc    780
atggaaaaca ggcccacgct atcgccaagc tcaagatccg aagcttaagt atggagaacc    840
atgaggtata aaaagtctcg ttgtccaggg ctttcaggga attcttcaac ccaaatcac    900 tgctttcatt cgtttgcttt ccttgtctct gttgaacagg ccctatacat tcatttattc    960
attctcgtac gttctgttga ccagaaccca ttcattcact atgcatttcc aacttctcgg   1020
cctcgccgcc ctcggctctc tcgccgctgc tgctcccgcc ccttctcgca cctctgaact   1080
ggttgagaga ggctcttctt gcactttcac ctccgctgct caggcctctg cgagcgccaa   1140
gagctgctcc aacatcgtcc tcaagaacat cgctgtccct gctggagaga ctcttgacct   1200
gtccaaggcc aaggacggtg ccaccgtacg ttcaaccaac tgcacaatat tcagtacacg   1260
acagattagt taattcaatc catcttttag atcaccttcg agggcaccac caccttcggc   1320
tacaaggaat ggaagggacc cctgatccgt ttcggtggta acaaaatcac cgtcacccag   1380
gccgccggcg ctgtcattga cggccagggc tcccgctggt gggacggcaa gggcaccaac   1440
ggtggcaaga ccaagcccaa gttcatctac gcccacaagc tccagtcctc gaccatcaag   1500
ggtttgcacg ttaagaactc ccccgtccag gtcttcagcg tccagggtaa cgacgtccac   1560
ctgaccgaca tcaccatcga caactcggat ggtgacaaca atggtggtca caacaccgat   1620
gctttcgacg ttagcgagag taacggtgtc tacatcaccg tgccaatgt caagaaccag    1680 gatgactgcc tggccatcaa ctctggtgag gtaagtagct cagaatactt tcatccccct   1740
tgacgcacag atattgacat ggcacagaac atcgaattca ccggcgctac ctgctccggc   1800
ggtcacggta tctccatcgg ttccatcggt aaccgcgaca gcaacaccgt caagaacgtc   1860
aaggttgccg actccaccgt cgtcgactcc gacaacggta tccgtatcaa gaccatctct   1920
ggtgctaccg gctctgtcag cggcgtgacc tacgagaaca tcaccctcaa gaacatcaag   1980
aagaacggta tcgtcatcga gcaggactac aagaacggtg gccccaccgg caagcccacc   2040
```

| | |
|---|---|
| accggtgtcc ccatcactga cctcactgtc aacggtgtca ctggctccgt tgccagcaag | 2100 |
| gccaccccg tctacatcct ctgcggcaag ggcagctgct ctgactggac ctggaagggt | 2160 |
| gtcagcatct ccggtggcaa gaagtctgat aagtgccaga acattccttc tggcgcttct | 2220 |
| tgctaagcga acaatgcttg atcgcgtgtt tggctctggt gtatagatac ccagggcgca | 2280 |
| ggccactctc aattacttta cttggtgtac catagatata tatgtcatat aatataagta | 2340 |
| tcaacatctg gctgtgtaca catatttttc tataaatatt ttgttcagtt attgtataca | 2400 |
| ttatctgttt gtagaactca tgctactacg gaatgtataa cggcaaagat cgagttcgaa | 2460 |
| tagcatatcc agtacacaaa cctgtctaac ccacggatat agagagtact tgaagcaatc | 2520 |
| aaagccttcc atcatcctcc agcgagaccg caaaagttct aatatatcgg gatccgttaa | 2580 |
| cggaaagcgt gtctgtactt cattccgata cttctataat tcaggattta ctgcctatac | 2640 |
| gggggttgag tcattagcga ctcattggcg actcacgtaa tatacctggc ccatagtaat | 2700 |
| tactttcaac aggacaaaaa aaaatgcgag gaactggaga caaactatta tctaaccagc | 2760 |
| tatccatagt ggttcttacg atccatcatg catgatggac gatattccga aaatggaaat | 2820 |
| agactaaccc caatatcggg agtgttgtca gtccaggacc gagccttcgg ttagcgttat | 2880 |
| ttctgtgttc tcatgaatag tcgctcttat tggacgaaat ggcaatgcgc taactccaat | 2940 |
| gtcgggtca tgtcttggca tatcgaatct ctttctatac ggtcgacaag attctggata | 3000 |
| aataaggtcg gcacgaccca ttgaccgcag aaagctttca ctaactgttt tgtcactaag | 3060 |
| gaacatacgg tcttcgtcgc atcgcaccat gcctgacgaa gaaaagaata acagcctgt | 3120 |
| gggtgctacc tgaactcgta gtggatatct actcacggca aggttgatag gaaccggcag | 3180 |
| ctggtcggga gacatatccg ctgatggaca tgggaaatgg catagt | 3226 |

<210> SEQ ID NO 3
<211> LENGTH: 2728
<212> TYPE: DNA
<213> ORGANISM: Aspergillus oryzae

<400> SEQUENCE: 3

| | |
|---|---|
| ctttcggggg aatcccgaca ccgacttaga tcattatcgg gcttcgcgag atatgaaaaa | 60 |
| tgttcctgac tctggcagtc atgtaatgct actctctatc atggaaactt catcttatag | 120 |
| atcatggtct agaactcggc atgcagctgt gtgccgtatt gggggttac agagtcagac | 180 |
| catttaacct tggcttgatc atatctgctt ggcatgctgg caggcgaact atgtaatgct | 240 |
| tatgcgaacc ttatgacctt ctacttagcg tcagcgcaac ctatgctaat caagtacaat | 300 |
| atacactttt cgagatgcct acctatgtag acaactgttg agttggtgga acaaggtaga | 360 |
| agatgagggg ggatttacca aaccatttta caaataccat gatcactatc ccgtcggcct | 420 |
| cgtatttttt taattgcagg acatactcca tcctaactcc caggatattc cgttacggcg | 480 |
| agtcaggcat gaaatgctgg tggtttggcc catgcttcag tcgactaccg acacgctacc | 540 |
| ctgagcttgg cagagacctc ttgtcgaaaa gtggagcaaa actagagccg ggagacttca | 600 |
| gcatagggaa tgcggtccga tagcccatac ccacatagca cttggctcgg acccgccagg | 660 |
| agccaatagg ggataaaaca tggccacatg cgagttaaga atatgccgct gggaatgcgc | 720 |
| attgggcggt ggccggataa attgcgggtt tggatcgtga gatgaaacaa aagtccgtcc | 780 |
| ggcaatttag gtggatattg ttccggaaag ccctaggtgt ccaggagcca caaggcttga | 840 |
| ttcttgaaac aataaactct attctaggcc atttagtcgt ttcggataga catgcagaag | 900 |

```
gtcgatgcgg tagctataaa ggggactctg tttccttgcc attgacagtg gtcatcagtg    960
attcttccag cttacacacc acaagaccaa caccgtcgcc atggttagct tctcttctct   1020
cctccttgcc gtttccgctg tctccggcgc tttggctgcc cctggcgatt ccactcttgt   1080
tgagctcgcc aagcgcgcta tcaccagctc cgagacaggc accaacaacg gctactacta   1140
ctccttctgg accaacggcg gtggtgatgt cgaatacacc aatggcaacg gcggccagta   1200
cagcgtcaaa tggaccaact gcgacaactt tgtcgccgga aagggatgga accccggcag   1260
tgcgaagtat gataccccctc gaaagatccc atccaagccc acagacacta acagcagtgt   1320
gttactagga ctgtgaccta cagcggtgag tgggagagca acagcaacag ctacgtctct   1380
ctctacggct ggacccagaa ccccctcgtc gaatactaca tcgttgacaa gtacggcgac   1440
tacgatccct ccaccggcgc taccgagctt ggcaccgtcg agagcgatgg cggcacctac   1500
aagatctaca agactactcg tgaaaacgct ccctccattg agggcacctc gaccttcaac   1560
cagtactggt cggtccgcca gagcggccgt gttggtggca ccatcactgc tcagaaccac   1620
ttcgatgcct gggccaacgt tggttttgca gttgggtacc ataactacat gatccttgcc   1680
accgagggct acaagagcag cgggtctgcc actatcactg ttgagtaaat ggggttgtct   1740
ttagttgcgg gataccgtgg tcaacttgct ttgtaggggtg atccgccgtg atatttttc   1800
ccttcatatg gactcggatt ccgggtttat attcttcttg tcaactgccg gagatcccgt   1860
aattggtgtc tctttctggt gtcgccgtgt acatagtcac atttgtcctt tcttggccct   1920
ttcgtcagag aaatccatgc tttcacaagc ccagttctcc ttgcgttaaa agtctttgct   1980
gattagtgtg gacactaacg gatcggaccc caattaagtc caccaaatac gagcggagaa   2040
cagaggacat acacgttcaa tatccaagca agcattaat gctgtcgatc gattagatta   2100
aaaccaacca tctgtagcat atcttccaat ggcaaagctt cccacaacgt tcagtcactt   2160
gttcctagct ctaaggagcc gaaccgttct caggccaccc acgcgagtcc gcaatgacac   2220
gcaacacgtt aatgaagtcc taaagtcttt tccgaaaggc taggcagtgc ccaaagcgcc   2280
tgatggttat aaaagttcac catcatcggt gcggggtcaa gcatgcattg actactaata   2340
aacactcttg caatcacata cctcgcacca tggaactgat cgaacgatgt gtatacaacc   2400
ccccgacgcc gccaaaacgg acgcgcgaga aaccgatgaa ggtgctcgca ctgggtatgt   2460
cccggtcggg gacagagtct ctctcgcgtg ccctccgcat cctcgggtac gatcatgtct   2520
tccacggctt cgaaatgtgg gaaagtacac caatgctctg gaggtcgtgg acgatgctag   2580
gacgacggaa atggggcaat gctggtactg ctggtggaag gtccaacatt acgagggagg   2640
atttcgacaa cttattcggc cattgcgagg ctatcaccga ccagccaggt acactcttcg   2700
ccccggaatt gatttccgct tatcccga                                      2728
```

<210> SEQ ID NO 4
<211> LENGTH: 3767
<212> TYPE: DNA
<213> ORGANISM: Aspergillus oryzae

<400> SEQUENCE: 4

```
aaattgtaaa attggctcag cctccactgc cttgaagtct tgtcagggg agccgggtat     60
atactcttcc gtaactctga gtataatgtt tggtactcgt caattgtccc tatcgttcgt    120
tgttcaaatg ttgatcgacc ttcgttaaca gtccataatc ggttgccctg ttctgtaaac    180
gtatttggga gccgctcagc atttttccgcc ttggtatagg tcttcttgtt gtaggtatac    240
aatgctacga tgttgaggct gatggtacct gatgctcgga gataaaaaat taaacacaac    300
```

```
acgttaggta acgtttgatg caatttgccc ctgatcaacg attggaactg gaggtgattg    360
gagaccaaat tcttcagcat cttatctttg attgttaact ccgagggctc gggaatagtt    420
acccgtttcc tcttagcgga tgcaatagag caagaaaacg tgccaaaata ctcaagaaag    480
accgcgtcag acaagatgag tgccaagaga gagccaaatc tcggtcattg tatctcccct    540
gaatgttgct gacatggtgg ctcgatcatg gatagctttg cacgcgcaag ggtcagggct    600
gcatggagag atcagataag gccggatctc agccgaaccg gaacatcaga taacaaaaat    660
tcatcgtcgg acgaccggag actactacta ctactagtat caactccgcg gtcgagcct     720
cgaggaagac cttttgactt ggcatcttgc cacgcaaccc ggtgacgaca gcctgagtag    780
aattaaggat ggcaaagcgt tgatctgccg tttggtccac aagcttgtta cgaatcccga    840
acctatgat gccgaagacg gtggtctctc agccctagcc ttgcaataaa taggacgata     900
gtttccctat ggctcctcct agatacgacc tcatcattcg tttattcctt tcgtatcctt    960
tgaacactcc ttgacctctg ccattctttt ggttcgaaag atgcgccaac actcgcgcat    1020
ggccgttgct gctttggcag caggagcgaa cgcagcttct tttaccgatg tgtgcaccgt    1080
gtctaacgtg aaggctgcat tgcctgccaa cggaactctg ctcggaatca gcatgcttcc    1140
gtccgccgtc acggccaacc ctctctacaa ccagtcggct ggcatgggta gcaccactac    1200
ctatgactac tgcaatgtga ctgtcgccta cacgcatacc ggcaagggtg ataaagtggt    1260
catcaagtac gcattcccca gccctccga ctacgagaac cgtttctacg ttgctggtgg     1320
tggtggcttt tccctctcta gcgatgctac cggaggtctc gcctatgcg ctgtgggagg     1380
tgccaccgat gctggatacg acgcattcga taacagctac gacgaggtag tcctctacgg    1440
aaacggaacc attaactggg acgccacata catgttcgca taccaggcac tgggagagat    1500
gacccggatc ggaaagtaca tcaccaaggg cttttatggc cagtccagcg acagcaaggt    1560
ctacacctac tacgagggtt gctccgatgg aggacgtgag ggtatgagtc aagtccagcg    1620
ctggggtgag gagtatgacg gtgcgattac tggtgccccg gctttccgtt tcgctcagca    1680
acaggttcac catgtgttct cgtccgaagt ggagcaaaact ctggactact acccgcctcc    1740
atgtgagttg aagaagatcg tgaacgccac cattgctgct tgcgacccgc ttgatggaag    1800
aaccgacggt gttgtgtccc ggacggatct ttgcaagctt aacttcaatt tgacctctat    1860
catcggtgag ccttactact gtgctgcggg aactagcact tcgcttggtt tcggcttcag    1920
caatggcaag cgcagcaatg tcaagcgtca ggccgagggc agcaccacca gctaccagcc    1980
cgcccagaac ggcacggtca ccgcacgtgg tgtagctgtc gcccaggcca tctacgatgg    2040
tctccacaac agcaagggcg agcgcgcgta cctctcctgg cagattgcct ctgagctgag    2100
cgatgctgag accgagtaca actctgacac tggcaagtgg gagctcaaca tcccgtcgac    2160
cggtggtgag tacgtcacca agttcattca gctcctgaac ctcgacaacc tttcggatct    2220
gaacaacgtg acctacgaca ccctggtcga ctggatgaac actggtatgg tgcgctacat    2280
ggacagcctt cagaccaccc ttcccgatct gactcccttc caatcgtccg gcggaaagct    2340
gctgcactac cacggtgaat ctgaccccag tatccccgct gcctcctcgg tccactactg    2400
gcaggcggtt cgttccgtca tgtacggcga caagacggaa gaggagccc tggaggctct     2460
cgaggactgg taccagttct acctaatccc cggtgccgcc cactgcggaa ccaactctct    2520
ccagcccgga cctacccctg agaacaacat ggagattatg atcgactggg tcgagaacgg    2580
caacaagccg tcccgtctca atgccactgt ttcttcgggt acctacgccg gcgagaccca    2640
```

-continued

```
gatgctctgc cagtggccca agcgtcctct ctggcgcggc aactccagct tcgactgtgt    2700
caacgacgag aagtcgattg acagctggac ctacgagttc ccagccttca aggtccctgt    2760
atactagtgt gcttgtatta ttacttgcga ccatctccta tatggagtga cgagatttgg    2820
ggatccctta gcttcttagt gaagttaatc ttcccaactt ttattcttca tttcatgctt    2880
gctgagcaac tggctctttt gtctatacat tttaagtatt aaaccttggt tgagtgtaaa    2940
tactcaaact ggggtcaacc gagacaaact tattttctt ctttccacga aacattccat     3000
cgagcttgta catagataat cgcataagac caatatcaca gtgaagacca cttcaccata    3060
accacacgca aaagcccacc aacagacagt aaccctcttc atcttaaaat attgattacc    3120 tattttaaa cattacatac taatcaaccc cttaaacccg catcaaagcc ccaaaaaccc     3180
cctcttcctc cccttagcag acctagacct ggacctggac cgtctcgaga tggccgaatt    3240
cctcgtatta acacgatcga tatcatacgg attagcctca taacccgcat tcccgtcacg    3300
catagtcgac agcgagctcc tacccccaga ctccaacctc cccaaatcct gtcctccatc    3360
agcactcccc ctcccctcag cctggaccct aacctcctca tcaacagcct tctcctcctc    3420
ccccagagag accgtcttct ccgccaacct cctcataaaa tcatccgcct cggcggcata    3480
tttacacttc ctccgtataa cagccccata cttataaaaa acaaagggaa aaggcacaca    3540
agcaagagcc agaaaagcag gaatgcagga agcccaatgg acgcccagat tgcgatacat    3600
gtaagtcgtg aagaggggga atccggcacc gaaacaggat ctgataattg agtttgcggc    3660
cagcacgcta gcagcgtaga tagtatatgc atcgataaga taggacatga tattgaggaa    3720
gacaagaacc ataccgaagc cgaagggggc ggcggcgatg atactga                  3767
```

<210> SEQ ID NO 5
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 5
atctcgcagt cccgattcgc ctatc                                           25

<210> SEQ ID NO 6
<211> LENGTH: 27
<212> TYPE: DNA
<213> ORGANISM: Artificial Sequence
<220> FEATURE:
<223> OTHER INFORMATION: synthesized oligonucleotide

<400> SEQUENCE: 6
aaatgccttc tgtggggttt attgttc                                         27

<210> SEQ ID NO 7
<211> LENGTH: 47
<212> TYPE: DNA
<213> ORGANISM: Artificial Sequence
<220> FEATURE:
<223> OTHER INFORMATION: synthesized oligonucleotide

<400> SEQUENCE: 7
gaacaataaa ccccacagaa ggcatttatg gcggtcctta gcgtgct                   47

<210> SEQ ID NO 8
<211> LENGTH: 47
<212> TYPE: DNA
<213> ORGANISM: Artificial Sequence

```
<220> FEATURE:
<223> OTHER INFORMATION: synthesized oligonucleotide

<400> SEQUENCE: 8
gcagtaccat catatactct ccaccctgag gagaggaagg atgggag              47

<210> SEQ ID NO 9
<211> LENGTH: 27
<212> TYPE: DNA
<213> ORGANISM: Artificial Sequence
<220> FEATURE:
<223> OTHER INFORMATION: synthesized oligonucleotide

<400> SEQUENCE: 9
agggtggaga gtatatgatg gtactgc                                    27

<210> SEQ ID NO 10
<211> LENGTH: 24
<212> TYPE: DNA
<213> ORGANISM: Artificial Sequence
<220> FEATURE:
<223> OTHER INFORMATION: synthesized oligonucleotide

<400> SEQUENCE: 10
cccacattga agaagcagct cctc                                       24

<210> SEQ ID NO 11
<211> LENGTH: 48
<212> TYPE: DNA
<213> ORGANISM: Artificial Sequence
<220> FEATURE:
<223> OTHER INFORMATION: synthesized oligonucleotide

<400> SEQUENCE: 11
gaacaataaa ccccacagaa ggcatttatg catttccaac ttctcggc             48

<210> SEQ ID NO 12
<211> LENGTH: 47
<212> TYPE: DNA
<213> ORGANISM: Artificial Sequence
<220> FEATURE:
<223> OTHER INFORMATION: synthesized oligonucleotide

<400> SEQUENCE: 12
gcagtaccat catatactct ccaccctgtt tgtctccagt tcctcgc              47

<210> SEQ ID NO 13
<211> LENGTH: 30
<212> TYPE: DNA
<213> ORGANISM: Artificial Sequence
<220> FEATURE:
<223> OTHER INFORMATION: synthesized oligonucleotide

<400> SEQUENCE: 13
ccaacgacga ctgtctcatt actagtctac                                 30

<210> SEQ ID NO 14
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 14
gtcgactaac ttggaggacg gaaga                                      25
```

<210> SEQ ID NO 15
<211> LENGTH: 45
<212> TYPE: DNA
<213> ORGANISM: Artificial Sequence
<220> FEATURE:
<223> OTHER INFORMATION: synthesized oligonucleotide

<400> SEQUENCE: 15
tcttccgtcc tccaagttag tcgacatgcg ccaacactcg cgcat            45

<210> SEQ ID NO 16
<211> LENGTH: 49
<212> TYPE: DNA
<213> ORGANISM: Artificial Sequence
<220> FEATURE:
<223> OTHER INFORMATION: synthesized oligonucleotide

<400> SEQUENCE: 16
ggtagacgtc atataatcat acggttcatc gatcgtgtta atacgagga        49

<210> SEQ ID NO 17
<211> LENGTH: 32
<212> TYPE: DNA
<213> ORGANISM: Artificial Sequence
<220> FEATURE:
<223> OTHER INFORMATION: synthesized oligonucleotide

<400> SEQUENCE: 17
atgaaccgta tgattatatg acgtctacca gc                          32

<210> SEQ ID NO 18
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 18
cgagtgagcc gtccctcaat aactt                                  25

<210> SEQ ID NO 19
<211> LENGTH: 47
<212> TYPE: DNA
<213> ORGANISM: Artificial Sequence
<220> FEATURE:
<223> OTHER INFORMATION: synthesized oligonucleotide

<400> SEQUENCE: 19
tcttccgtcc tccaagttag tcgacatggt tagcttctct tctctcc          47

<210> SEQ ID NO 20
<211> LENGTH: 49
<212> TYPE: DNA
<213> ORGANISM: Artificial Sequence
<220> FEATURE:
<223> OTHER INFORMATION: synthesized oligonucleotide

<400> SEQUENCE: 20
ggtagacgtc atataatcat acggttcatc gtgttgcgtg tcattgcgg         49

<210> SEQ ID NO 21
<211> LENGTH: 45
<212> TYPE: DNA
<213> ORGANISM: Artificial Sequence
<220> FEATURE:
<223> OTHER INFORMATION: synthesized oligonucleotide

<400> SEQUENCE: 21
tcttccgtcc tccaagttag tcgacatggc ggtccttagc gtgct                                45

<210> SEQ ID NO 22
<211> LENGTH: 49
<212> TYPE: DNA
<213> ORGANISM: Artificial Sequence
<220> FEATURE:
<223> OTHER INFORMATION: synthesized oligonucleotide

<400> SEQUENCE: 22
ggtagacgtc atataatcat acggttcatg aggagaggaa ggatgggag                            49

<210> SEQ ID NO 23
<211> LENGTH: 26
<212> TYPE: DNA
<213> ORGANISM: Artificial Sequence
<220> FEATURE:
<223> OTHER INFORMATION: synthesized oligonucleotide

<400> SEQUENCE: 23
gcactgtatt ggtatgtgaa cgccag                                                     26

<210> SEQ ID NO 24
<211> LENGTH: 24
<212> TYPE: DNA
<213> ORGANISM: Artificial Sequence
<220> FEATURE:
<223> OTHER INFORMATION: synthesized oligonucleotide

<400> SEQUENCE: 24
caagcatctg cttcgactcc ttcg                                                       24

<210> SEQ ID NO 25
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 25
ggtgacgatg agccgctctt                                                            20

<210> SEQ ID NO 26
<211> LENGTH: 21
<212> TYPE: DNA
<213> ORGANISM: Artificial Sequence
<220> FEATURE:
<223> OTHER INFORMATION: synthesized oligonucleotide

<400> SEQUENCE: 26
gggcaattga ttacgggatc c                                                          21

<210> SEQ ID NO 27
<211> LENGTH: 22
<212> TYPE: DNA
<213> ORGANISM: Artificial Sequence
<220> FEATURE:
<223> OTHER INFORMATION: synthesized oligonucleotide

<400> SEQUENCE: 27
tccaccttta tttggagggg ct                                                         22

<210> SEQ ID NO 28

<211> LENGTH: 4044
<212> TYPE: DNA
<213> ORGANISM: Aspergillus oryzae

<400> SEQUENCE: 28

```
cttaaaaatc gatctcgcag tcccgattcg cctatcaaaa ccagtttaaa tcaactgatt      60
aaaggtgccg aacgagctat aaatgatata acaatattaa agcattaatt agagcaatat     120
caggccgcgc acgaaaggca acttaaaaag cgaaagcgct ctactaaaca gattactttt     180
gaaaaaggca catcagtatt taaagcccga atccttatta agcgccgaaa tcaggcagat     240
aaagccatac aggcagatag acctctacct attaaatcgg cttctaggcg cgctccatct     300
aaatgttctg gctgtggtgt acaggggcat aaaattacgc actacccgaa tcgatagaac     360
tactcatttt tatatagaag tcagaattca tggtgttttg atcattttaa attttatat     420
ggcgggtggt gggcaactcg cttgcgcggg caactcgctt accgattacg ttagggctga     480
tatttacgta aaaatcgtca agggatgcaa gaccaaagta gtaaaacccc ggagtcaaca     540
gcatccaagc ccaagtcctt cacgagaaa ccccagcgtc cacatcacga gcgaaggacc     600
acctctaggc atcggacgca ccatccaatt agaagcagca aagcgaaaca gcccaagaaa     660
aaggtcggcc cgtcggcctt ttctgcaacg ctgatcacgg gcagcgatcc aaccaacacc     720
ctccagagtg actaggggcg gaaatttaaa gggattaatt tccactcaac cacaaatcac     780
agtcgtcccc ggtattgtcc tgcagaatgc aatttaaact cttctgcgaa tcgcttggat     840
tccccgcccc tggccgtaga gcttaaagta tgtcccttgt cgatgcgatg tatcacaaca     900
tataaatact agcaagggat gccatgcttg aggatagcaa accgacaaca tcacatcaag     960
ctctcccttc tctgaacaat aaacccccaca gaaggcattt atgatggtcg cgtggtggtc    1020
tctatttctg tacggccttc aggtcgcggc acctgctttg gctgcaacgc ctgcggactg    1080
gcgatcgcaa tccatttatt tccttctcac ggatcgattt gcaaggacgg atgggtcgac    1140
gactgcgact tgtaatactg cggatcaggt gtgttgttac ctactagctt tcagaaagag    1200
gaatgtaaac tgacttgata tagaaatact gtggtggaac atggcagggc atcatcgaca    1260
aggtaaattg ccccttttatc aaaaaaaaag aaggaaaagc agaagaaaaa taaaataaaa    1320
agaactctag tcctaaccat cacatagttg gactatatcc agggaatggg cttcacagcc    1380
atctggatca cccccgttac agcccagctg ccccagacca ccgcatatgg agatgcctac    1440
catggctact ggcagcagga tatgtaagtc gatttcttta aatatctacc tgtcatcttt    1500
tacatcaata tgaactaact tgatggtttt agatactctc tgaacgaaaa ctacggcact    1560
gcagatgact tgaaggcgct ctcttcggcc cttcatgaga gggggatgta tcttatggtc    1620
gatgtggttg ctaaccatat ggttcgtggt cctttgcaac tgacttcgcg gatatggttc    1680
atttcagtac tgacaatgag taatatcagg gctatgatgg agcgggtagc tcagtcgatt    1740
acagtgtgtt taaccgttc agttcccaag actacttcca cccgttctgt ttcattcaaa    1800
actatgaaga tcagactcag gttgaggatt gctggctagg agataacact gtctccttgc    1860
ctgatctcga taccaccaag gatgtggtca agaatgaatg gtacgactgg gtgggatcat    1920
tggtatcgaa ctactccagt aagatatttc tccctcattc tacaacttgg ctgatcgatg    1980
atacttacga aatcagttga cggcctccgt atcgacacag taaaacacgt ccagaaggac    2040
ttctggcccg ggtacaacaa agccgcaggc gtgtactgta tcggcgaggt gctcgacggt    2100
gatccggcct acacttgtcc ctaccagaac gtcatggacg cgtactgaa ctatcccatg    2160
tatggttcct ccaaccatga gccttcttgc aagtctcatc tcctaacgaa acggctaaaa    2220
```

-continued

```
ccagttacta tccactcctc aacgccttca agtcaacctc cggcagcatg acgacctct    2280 acaacatgat caacaccgtc aaatccgact gtccagactc aacactcctg ggcacattcg    2340
tcgagaacca cgacaaccca cggttcgctt cgtaagtctt ccctttttatt ttccgttccc    2400 aatttccaca cagaacccca cctaacaaga gcaaagttac accaacgaca tagccctcgc    2460
caagaacgtc gcagcattca tcatcctcaa cgacggaatc cccatcatct acgccggcca    2520
agaacagcac tacgccggcg aaacgaccc cgcgaaccgc gaagcaacct ggctctcggg    2580
ctacccgacc gacagcgagc tgtacaagtt aattgcctcc gcgaacgcaa tccggaacta    2640
tgccattagc aaagatacag gattcgtgac ctacaaggta agcacaacct ctaagcatac    2700
cctaatggcc tatcttcaga gtatctgaca caagagacta atcactggca atacagaact    2760
ggcccatcta caaagacgac acaacgatcg ccatgcgcaa gggcacagat gggtcgcaga    2820
tcgtgactat cttgtccaac aagggtgctt cgggtgattc gtataccctc tccttgagtg    2880
gtgcgggtta cacagccggc cagcaattga cggaggtcat tggctgcacg accgtgacgg    2940
ttggttcgga tggaaatgtg cctgttccta tggcaggtgg gctacctagg gtattgtatc    3000
cgactgagaa gttggcaggt agcaagatct gtagtagctc gtgaagggtg gagagtatat    3060
gatggtactg ctattcaatc tggcattgga cagtgagttt gagtttgatg tacagttgga    3120
gtcgttactg ctgtcatccc cttatactct tcgattgttt ttcgaaccct aatgccaagc    3180
acgctagtct attataggaa aggatccgga ttaatgtgtt ttcataacgc ggtactgtat    3240
ggtacttctg tattatatca ccgaagctca tgtatcttac atgtatatat tatacagaca    3300
caaccttggt taccccacca tgatgtttcc tgcagataat ctcctgacga tcaatcttac    3360
cacagggata tgatggcacc caacctggcg ccttcgcaac atcaaattat ttgtgatatg    3420
atcaagtgcg atccatcact tactaatgcc cagatagctg aagctgctaa ctgcagcaca    3480
cgcgcaattc ctaggattcg gtcaaatctc cggctattcg gcagtagcaa agcccctcca    3540
aataaaggtg gacgcccacg aagcatctca ccaataatgc tggaggctct tgtgatcat    3600 cttcttgaaa agcctgatct ataccttgac gaaatggcca tctttctatg ggatgagttc    3660
caaatatacg caactacatc tagtatcagg cgggctctgt cttctaaagg ttggtccaaa    3720
aaggcagctc ggcagaaagc aaaggaacgg aattcagatc tgcgggatat gtatttccat    3780
ttaatctcag attttcattc ctatcagctt gtatacgtgg acgaatctgg atgcgataaa    3840
cgagctggct tccgacgaac gggctggtct cctctaggta caactcctat tcaagtgtct    3900
aaatttcatc gtgatcagcg gtatcaaata ttgcctgcat attctcaaga cggtatcatt    3960
ctgtcccgta tctttcgagg tgcgaccgat acttcagtct tgaggatttt tattgaggag    4020
ctgcttcttc aatgtgggaa atgg                                          4044
```

<210> SEQ ID NO 29
<211> LENGTH: 3570
<212> TYPE: DNA
<213> ORGANISM: Aspergillus oryzae

<400> SEQUENCE: 29

```
cggacaaggg aataacttcc aatggacacc gataatgata tattagtcgt taactatcat      60
cccctagacc gacgattcgt ccatcctttc atatgtacat atacacatag actagtatac     120
ctatcaagtc gactccggtt ctaaccaagg catagtatac ataaaatggt ctactaccaa     180
ggtaccccag aaacaagaat gtgaatctct tagtaactat ggagggcaag cattaattta     240
```

```
cccgctttac cccgagggaa tgcggaagat ctcgcggcag ggttgacaca gttgacagag      300
agctcagcca gcgagagtca cagaagactg atgagcccca ccatttcatt ggaaagattc      360
gggaggacga ggtcgagagc ttttgccggg gtagaggacg aggatggtac aagaactaga      420
cctttccaac tttaattgtt gacacctatt taattctctc cttcttcttt attttatttt      480
tcatttctcc aacgacgact gtctcattac tagtctacta gtaactctgt cttatcgtca      540
tctcccatag gtgagtttgg ttgttttgtt tccactgaga tcatgacctc ctcctacccc      600
accatcccac tattttttgtt acggtagcca tgacccctcc atggcaaaga gagaggagga      660
cgaggacgat caggaaactg tgtctcgccg tcataccaca atcgtgttat cctgattgac      720
atcttcttaa atatcgttgt aactgttcct gactctcggt caactgaaat tggatctccc      780
caccactgcc tctaccttgt actccgtgac tgaaccatcc gatcattctt tttgggtcgt      840
cggtgaacac aaccccgct gctagtctcc ttccaacacc gatccagaat tgttttgatt      900
ttccattccc ttcgtttata tctgtcgtct ctcctccctt tccgtctctt ttcttccgtc      960
ctccaagtta gtcgactgac caattccgca gctcgtcaaa atgcctatca ccaagatcca     1020
cgcccgctct gtttacgact cccgcggtaa ccctaccgtt gaggtggacg ttgtcaccga     1080
gactggtttg caccgcgcta tcgttccctc tggtgcttcc actggttagt gacccgcatt     1140
atgtactccc tcgtcctcgt tctatcatgc tgacgatcaa acactaggtc agcacgaggc     1200
ccacgagctc cgtgacggtg acaagaccca ctggggtgga aagggtatgt attagatgct     1260
ccccgaatgc ttgtctggtg caacggaggc tgattgtacc gacggagaac aggtgttctc     1320
aaggctgtcg agaacgtcaa taagaccatt gcccccgccg tcatcgagga gaaccttgat     1380
gtcaaggacc agtccaaggt cgatgagttc ctcaaaaagc ttgatggatc tgctaacaag     1440
tctaacctcg gtgctaacgc catcctcggt gtcagcttgg ccattgccaa ggctggtgct     1500
gctgagaagg gtgtccctct ctatgctcac atctccgacc ttgctggtac taagaagccc     1560
tatgtgcttc ctgtcccctt ccagaacgtc ctgaacggtg ctctcacgc tggtggccgt     1620 ctggctttcc aggagttcat gattgttcct tcgtaagtac ccgggcccag gtcacgtgtc     1680
ataatcccct gcagctatac taacatggct gatagcgctg cccccctcttt ctccgaggct     1740 cttcgccagg gtgctgaggt ctaccagaag ctcaagactc tcgccaagaa gaagtacggc     1800
cagtctgctg gcaatgttgg tgacgagggt ggtgttgctc ccgatatcca gactgctgag     1860
gaggcacttg acctcatcac cgaggccatt gagcaggccg gttacactgg caagatgaag     1920
attgccatgg acgttgcttc cagcgaattc tacaaggctg atgtcaagaa gtacgacctt     1980
gacttcaaga acccgacag cgactcctcc aagtggctca cctacgagca actggccgac     2040
ctttacaaga ctcttgccag caagtacccc attgtcagca ttgaggaccc cttcgctgag     2100
gatgactggg aggcctggag ctacttctac aagacttctg acttccagat tgttgggtat     2160
gtaatcctct tccatttagt gtcatattcg aactgaatta acacgatctc cacagtgatg     2220
acttgaccgt caccaacccc ctgcgtatca agaaggccat cgagaccaag gcttgcaacg     2280
cccttctgct caaggtcaac cagatcggta ctcttaccga gtccatccag gctgccaagg     2340
actcctacgc tgacaactgg ggtgtcatgg tttccaccg ttccggtgag actgaggatg     2400
tcaccattgc cgatatcgct gtcggtctcc gctctggcca gatcaagacc ggtgctcctg     2460
cccgctctga gcgtctggcc aagctgaacc agatcctccg tatcgaggag agctgggca     2520 acaacgccat ctatgctggc gaaaagttcc gcacttctgt caacctgtaa atgaaccgta     2580
tgattatatg acgtctacca gccaacctga cacattatcg aaagatggtt ggactcggga     2640
```

```
ccacactgca tacccgggtt cccgctactt gcaacctctg agctgcacaa agcactacag    2700
atgatattct cttaagattt atgatgacga ttcgattagg ccagatatag tggcagtaat    2760
gcaataaaag tgccaaaaaa agtccctgcc catgtagacc gtcgctagta gctatagtct    2820
cccaatatac ttcgtagata tttactttat aatgtataat gatgttgact cctaatgaat    2880
gggcgtgaat ggtaagggta cacgtgaccc cgctagcccc accaccagat cgttttatcg    2940
tgaagttatt gagggacggc tcactcgccc acatcaaatt cgccttctgg ttattgattc    3000
acccacgacg accctcttgt tgggatacac ggcttactca ctctgttatt gagtcattag    3060
aagcttgaag cttttaccgc tttatacact cttgactagt catggcgccc gaacggtggg    3120
gtaagaagat ctgaaatttg tggccttccg catatagtct gctttcttta caacggcact    3180
ttactgacag ttcctacttt tctctcacag acgatgagga ggacagtgtc tcccctcctc    3240
ctgtggctcc tcgtcgcaga ttcgacgatg aagaagaaga tgaggtgggt taatctttct    3300
tttttgctat gtaccctact atatatggca catatgacca tcgcccggag acacaatttg    3360
ctaattagct gggatactca acaggtcctc gactcctggg acgccgctga agactccgaa    3420
gtagagcggg aaaaggcagc caaagcggcc gaagccaagg ctaaggccga cgccgaagct    3480
gccgcaaaga agaagagcaa gtcgcagcgt atacaggaac acaaggagga gcgcaaaaag    3540
aaggccgaag aggaggattc cgacagcgag                                    3570
```